US006930116B2

(12) United States Patent
Charifson et al.

(10) Patent No.: US 6,930,116 B2

(45) **Date of Patent: *Aug. 16, 2005**

(54) GYRASE INHIBITORS AND USES THEREOF

(75) Inventors: Paul Charifson, Framingham, MA (US); Dean Stamos, Framingham, MA (US); Michael Badia, Bedford, MA (US); Anne Laure Grillot, Cambridge, MA (US); Steven Ronkin, Watertown, MA (US); Martin Trudeau, Tewksbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 108 days.

This patent is subject to a terminal disclaimer.

(21) Appl. No.: 10/395,331

(22) Filed: Mar. 24, 2003

(65) Prior Publication Data

US 2004/0024030 A1 Feb. 5, 2004

Related U.S. Application Data

(60) Division of application No. 10/198,407, filed on Jul. 18, 2002, now Pat. No. 6,608,087, and a continuation of application No. PCT/US01/01374, filed on Jan. 16, 2001.

(60) Provisional application No. 60/254,331, filed on Dec. 8, 2000, and provisional application No. 60/176,671, filed on Jan. 18, 2000.

(51) Int. Cl.$^7$ .................... A61K 31/427; C07D 277/32

(52) U.S. Cl. ....................... 514/342; 514/340; 546/193; 546/194; 548/202

(58) Field of Search .......................... 514/318; 546/194

(56) References Cited

U.S. PATENT DOCUMENTS 5,925,659 A * 7/1999 Patchett et al. ............. 514/374

FOREIGN PATENT DOCUMENTS

EP 0 913 151 A1 5/1999

* cited by examiner

*Primary Examiner*—Joseph K. McKane
*Assistant Examiner*—Janet L Coppins
(74) *Attorney, Agent, or Firm*—Nandakumar Govindaswamy; Vertex Pharmaceuticals Incorporated

(57) ABSTRACT

The present invention relates to compounds of the formula I:

I

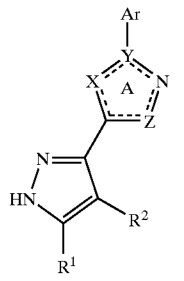

where Ring A is a thiazole, oxazole, imidazole or pyrazole and the substituents are as described in the specification, and pharmaceutically acceptable salts thereof. The compounds inhibit bacterial gyrase activity and therefore are useful for treating bacterial infections in mammals.

6 Claims, No Drawings

GYRASE INHIBITORS AND USES THEREOF

CROSS-REFERENCE TO RELATED APPLICATIONS

This application is a Divisional of U.S. application Ser. No. 10/198,407, filed on Jul. 18, 2002, now U.S. Pat. No. 6,608,087, and is a continuation of International Application Ser. No. PCT/US01/01374, filed on Jan. 16, 2001, which claims the benefit of Provisional Application No. 60/176,671, filed on Jan. 18, 2000 and Provisional Application No. 60/254,331 filed on Dec. 8, 2000, all which are being incorporated herein by reference.

TECHNICAL FIELD OF THE INVENTION

This invention is in the field of medicinal chemistry and relates to novel compounds, and pharmaceutical compositions thereof, that inhibit DNA gyrases. The invention also relates to methods of using the compounds and pharmaceutical compositions of this invention to treat bacterial infections, including nosocomial infections, that are susceptible to gyrase inhibition.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis,* and *Enterococcus*. The appearance of vancomycin resistant *enterococcus* was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., *Current Opinion in Anti-infective Investigational Drugs*, 1999, 1, 1; Levy, "The Challenge of Antibiotic Resistance", *Scientific American*, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in *The Medical Reporter*, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", *FDA Consumer* magazine, September, 1995).

As a result of the need to combat drug-resistant bacteria and the increasing failure of the available drugs, there has been a resurgent interest in discovering new antibiotics. One attractive strategy for developing new antibiotics is to inhibit DNA gyrase, a bacterial enzyme necessary for DNA replication, and therefore, necessary for bacterial cell growth and division. Gyrase activity is also associated with events in DNA transcription, repair and recombination.

Gyrase is one of the topoisomerases, a group of enzymes which catalyze the interconversion of topological isomers of DNA (see generally, Kornberg and Baker, *DNA Replication*, 2d Ed., Chapter 12, 1992, W. H. Freeman and Co.; Drlica, *Molecular Microbiology*, 1992, 6, 425; Drlica and Zhao, *Microbiology and Molecular Biology Reviews*, 1997, 61, 377). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (gyrA) and two B subunits (gyrB). Binding and cleavage of the DNA is associated with gyrA, whereas ATP is bound and hydrolyzed by the gyrB protein. GyrB consists of an amino-terminal domain which has the ATPase activity, and a carboxy-terminal domain which interacts with gyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase would be selective for this enzyme and be relatively inactive against the eukaryotic type II topoisomerases.

The widely-used quinolone antibiotics inhibit bacterial DNA gyrase. Examples of the quinolones include the early compounds such as nalidixic acid and oxolinic acid, as well as the later, more potent fluoroquinolones such as norfloxacin, ciprofloxacin, and gatifloxacin. These compounds bind to gyrA and stabilize the cleaved complex, thus inhibiting overall gyrase function, leading to cell death. However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

There are fewer known inhibitors that bind to gyrB. Examples include the coumarins, novobiocin and coumermycin A1, cyclothialidine, cinodine, and clerocidin. The coumarins have been shown to bind to gyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, *Trends in Microbiology*, 1997, 5, 102).

For coumarin-resistant bacteria, the most prevalent point mutation is at a surface arginine residue that binds to the carbonyl of the coumarin ring (Arg136 in *E. coli* gyrB). While enzymes with this mutation show lower supercoiling and ATPase activity, they are also less sensitive to inhibition by coumarin drugs (Maxwell, *Mol. Microbiol.*, 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, *Trends in Microbiology*, 1997, 5, 102). It would be desirable to have a new, effective gyrB inhibitor that overcomes these drawbacks. Such an inhibitor would be an attractive antibiotic candidate, without a history of resistance problems that plague other classes of antibiotics.

As bacterial resistance to antibiotics has become an important public health problem, there is a continuing need to develop newer and more potent antibiotics. More particularly, there is a need for antibiotics that represent a new class of compounds not previously used to treat bacterial infection. Such compounds would be particularly useful in treating nosocomial infections in hospitals where the formation and transmission of resistant bacteria are becoming increasingly prevalent.

DESCRIPTION OF THE INVENTION

It has now been found that compounds of this invention and pharmaceutical compositions thereof are useful in treating bacterial infections. These compounds have the general formula I:

I

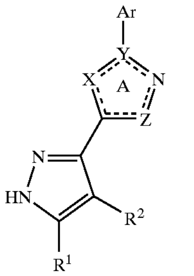

wherein:

$R^1$ is an optionally substituted group selected from a $C_{1-6}$ aliphatic group, $—C(R^4)_2(CH_2)_nNRCOR$, $—C(R^4)=N—OR$, $—C(R^4)=N—OC(=O)(C_{1-6}$ aliphatic), $—C(R^4)=NNRCO_2(C_{1-6}$ aliphatic), $—C(R^4)=NNRCOR$, $—C(R^4)=NN(R)_2$, $—C(R^4)_2(CH_2)_nNRCO_2(C_{1-6}$ aliphatic), $—CO_2(C_{1-6}$ aliphatic), $—CON(R)_2$, $—C(R^4)_2(CH_2)_nNCON(R)_2$, $—C(R^4)_2(CH_2)_nSO_2N(R)_2$, $—CONH—OR$, $—SO_2N(R)_2$, or $—C(R^4)_2(CH_2)_nNRSO_2(C_{1-6}$ aliphatic);

n is zero or one;

each R is independently selected from hydrogen or an optionally substituted $C_{1-6}$ aliphatic group;

$R^2$ is selected from hydrogen or, when $R^1$ is $—CO_2(C_{1-3}$ aliphatic) or $—CONH(C_{1-3}$ aliphatic), $R^2$ is further selected from -halo, —CN, $—C_{1-4}$ aliphatic, a three to five-membered heterocyclyl, or a five-membered heteroaryl;

Ring A is a heteroaryl ring selected from thiazole, oxazole, imidazole or pyrazole, wherein said imidazole is optionally attached by a $C_{1-3}$ bridge from an imidazole ring nitrogen to Ar to form a five- to seven-membered fused ring;

Z is $C—R^3$ or $N—R^3$;

$R^3$ is $—(CH_2)_pN(R^5)_2$ or an optionally substituted group selected from $C_{1-8}$ aliphatic, heterocyclyl, heterocyclylalkyl, aryl, aralkyl, heteroaryl, or heteroaralkyl;

each $R^4$ is indepependently selected from hydrogen, an optionally subtituted $C_{1-6}$ aliphatic group, or two $R^4$ taken together with the carbon to which they are attached form a three to six membered aliphatic ring;

each $R^5$ is independently selected from hydrogen, an optionally subtituted $C_{1-4}$ aliphatic group, or two $R^5$ taken together with the nitrogen to which they are attached form a five or six membered heterocyclic ring;

p is an integer from zero to four when Z is $C—R^3$ or an integer from one to four when Z is $N—R^3$; and Ar is an optionally substituted aryl, heteroaryl, or heterocyclyl ring.

As used herein, the following definitions shall apply unless otherwise indicated. The term "aliphatic" as used herein means straight chained, branched or cyclic $C_1$–$C_{12}$ hydrocarbons which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The term "alkyl" and "alkoxy" used alone or as part of a larger moiety refers to both straight and branched chains containing one to twelve carbon atoms. The terms "alkenyl" and "alkynyl" used alone or as part of a larger moiety shall include both straight and branched chains containing two to twelve carbon atoms. The terms "haloalkyl", "haloalkenyl" and "haloalkoxy" means alkyl, alkenyl or alkoxy, as the case may be, substituted with one or more halogen atoms. The term "halogen" means F, Cl, Br, or I. The term "heteroatom" means N, O or S. The nitrogen-containing compounds of this invention also include the corresponding N-oxides of the compounds as well as those having a quarternized form of any basic nitrogen.

Rings having one to four heteroatoms selected from N, O, or S include heterocyclic aromatic (or heteroaryl) rings and non-aromatic heterocyclic rings. Examples of aromatic heterocyclic rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, or 3-thienyl. Examples of non-aromatic heterocyclic rings include 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, tetrahydroisoquinoline, decahydroisoquinoline, and benzothiane.

An aryl group (carbocyclic and heterocyclic) or an aralkyl group, such as benzyl or phenethyl, may contain one or more substituents. Examples of suitable substituents on an unsaturated carbon atom of an aryl group include halogen, —R, —OR, —OH, —SH, —SR, protected OH (such as acyloxy), phenyl (Ph), substituted Ph, —OPh, substituted —OPh, substituted or unsubstituted five to six membered ring having one to four heteroatoms, $—NO_2$, —CN, $—NH_2$, —NHR, $—N(R)_2$, —NHCOR, —NHCONHR, $—NHCON(R)_2$, —NRCOR, $—NHCO_2R$, $—CO_2R$, $—CO_2H$, —COR, —CONHR, $—CON(R)_2$, $—S(O)_2R$, $—SONH_2$, —S(O)R, $—SO_2NHR$, or $—NHS(O)_2R$, where R is an aliphatic group or a substituted aliphatic group.

An aliphatic group or a non-aromatic heterocyclic ring may contain one or more substituents. Examples of suitable substituents on a saturated carbon of an aliphatic group or of a non-aromatic heterocyclic ring include those listed above for the unsaturated carbon as well as the following: =O, =S, =NNHR, $=NNR_2$, =N—OR, =NNHCOR, $=NNHCO_2R$, $=NNHSO_2R$, or =NR. An alkylidene chain is a hydrocarbon chain that may be saturated or unsaturated such as $—(CH_2)_n—$, $—(CH{=}CH)_m(CH_2)_n—$, or $—(C{\equiv}C)_m(CH_2)_n—$, where m and n are integers from zero to six. An alkylidene chain may be substituted in the same manner as an aliphatic group.

A substitutable nitrogen on an aromatic or non-aromatic heterocyclic ring may be optionally substituted. Suitable substituents on the nitrogen include R, COR, $S(O)_2R$, and $CO_2R$, where R is an aliphatic group or a substituted aliphatic group.

It will be apparent to one skilled in the art that certain compounds of this invention may exist in tautomeric forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

This invention also relates to a method of treating a bacterial infection in a mammal in need thereof, comprising the step of administering to said mammal a therapeutically effective amount of a compound having the formula I.

Subsets of compounds of this invention include I-A, I-B, I-C, I-D and I-E shown below:

I-A

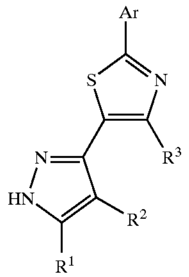

I-B

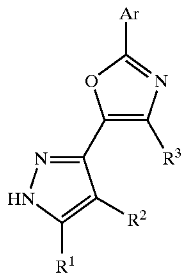

-continued

I-C

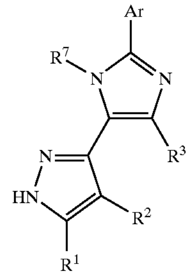

I-D

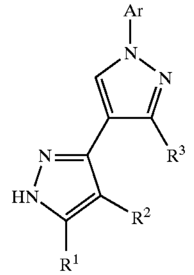

I-E

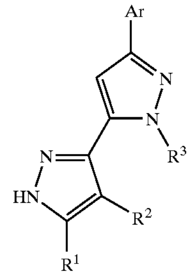

where $R^1$, $R^2$, $R^3$, and Ar are as described above and $R^7$ is hydrogen or a $C_{1-6}$ aliphatic group. Compounds of formula I-A are novel.

Preferred $R^1$ groups include $—C(R^4)_2NHCOR$, $—C(R^4)_2NHCO_2R$, $—CO_2R$, and —CONHR where R is an optionally substituted $C_{1-4}$ aliphatic group and each $R^4$ is independently selected from hydrogen, a $C_{1-3}$ alkyl group, or two $R^4$ taken together with the carbon to which they are attached form a three or four membered aliphatic ring. Examples of preferred R include $—C_{1-4}$ alkyl, $—C_{1-4}$ haloalkyl, -allyl, $—CH_2C{\equiv}CR^6$, $—CH(C_{1-3}\text{ alkyl})C{\equiv}CR^6$, and $—C(Me)_2C{\equiv}CR^6$, where $R^6$ is hydrogen, $—C_{1-4}$ aliphatic, $—CH_2N(Me)_2$, or $—CH_2O(C_{1-3}\text{ alkyl})$.

A preferred $R^2$ group is hydrogen. When $R^1$ is $—CONH(C_{1-3}\text{ alkyl})$ or $—CO_2(C_{1-3}\text{ alkyl})$, other preferred $R^2$ are halo, —CN and $—C_{1-4}$ alkyl groups.

Preferred $R^3$ groups include $C_{1-6}$ aliphatic optionally substituted by alkoxy, alkylamino or dialkylamino, optionally substituted morpholinyl, piperazinyl, piperidinyl, pyridyl, phenyl or benzyl.

Preferred Ar groups are aryl and heteroaryl groups including optionally substituted phenyl, pyridyl, and pyrimidinyl rings. Examples of optional substituents attached to Ar include one or more of the following: alkyl, alkoxy, hydroxy, carboxy, halo, $SO_2R$, $SO_2NHR$, amino, alkylamino, dialkylamino, and pyridyl.

Selected compounds of formula I are shown in Table 1 ($R^2$ is hydrogen). The numbering of these examples is based on the subsets described above: IA refers to ring A thiazoles (X is sulfur) IB to oxazoles (X is oxygen), IC to imidazoles (X is NH), ID to pyrazoles (Y is nitrogen) and IE to pyrazoles (Z is nitrogen).

TABLE 1
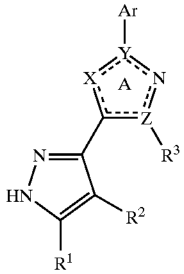
I
| No. | $R^3$ | $R^1$ | Ar |
|---|---|---|---|
| IA-1 | 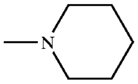 | $—CH_2NHCO_2Me$ | 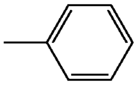 |
| IA-2 | 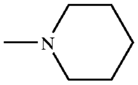 | $—CH_2NHCO_2Me$ | 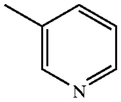 |
| IA-3 | 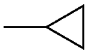 | $—CH_2NHCO_2—CH_2C{\equiv}CH$ | 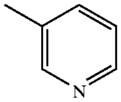 |
| IA-4 | 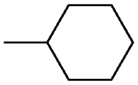 | $—CH_2NHCO_2—CH_2C{\equiv}CH$ | 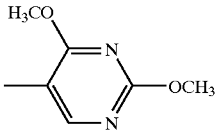 |
| IA-5 | 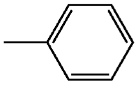 | $—CH_2NHCO_2—CH_2C{\equiv}CHCH_3$ | 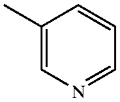 |
| IA-6 | 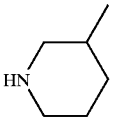 | $—CH_2NHCO_2—CH_2C{\equiv}CHCH_3$ | 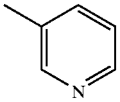 |
| IA-7 | 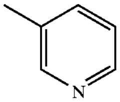 | $—CH_2NHCO_2—CH_2C{\equiv}CHCH_3$ | 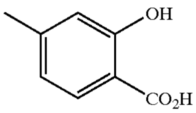 |
| IA-8 | 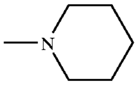 | —CONHEt | 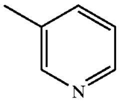 |
| IA-9 | 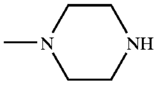 | $—CH_2NHCO_2Me$ | 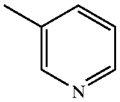 |
| IA-10 | $—(CH_2)_3CH_3$ | $—CH_2NHCO_2—CH_2C{\equiv}CH$ | 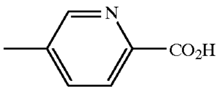 |

TABLE 1-continued
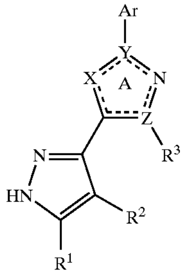
I
| No. | $R^3$ | $R^1$ | Ar |
| --- | --- | --- | --- |
| IA-11 | 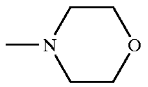 | $—CH_2NHCO_2—CH_2C{\equiv}CHCH_3$ | 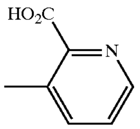 |
| IA-12 | $—CH_2NHEt$ | $—CH_2NHCO_2—CH_2C{\equiv}CH$ | 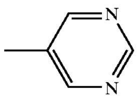 |
| IA-13 | $—N(Et)_2$ | $—CH_2NHCO_2—CH_2C{\equiv}CHCH_3$ | 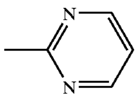 |
| IA-14 | 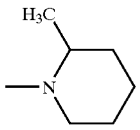 | $—CH_2NHCO_2—CH_2C{\equiv}CH$ | 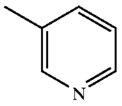 |
| IA-15 | 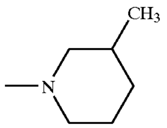 | $—CH_2NHCO_2Et$ | 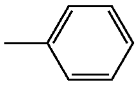 |
| IA-16 | 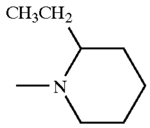 | $—CH_2NHCO_2—CH_2C{\equiv}CH$ | 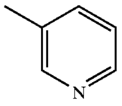 |
| IA-17 | 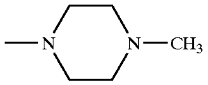 | $—CH_2NHCO_2—CH_2C{\equiv}CH$ | 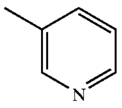 |
| IA-18 | 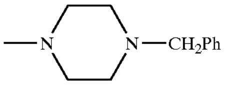 | $—CH_2NHCO_2Me$ | 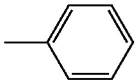 |
| IA-19 | $—CH_3$ | $—CH_2NHCO_2—CH_2C{\equiv}CHCH_3$ | 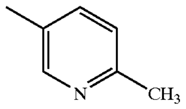 |
| IA-20 | $—CH_2OMe$ | $—CH_2NHCO_2—CH_2C{\equiv}CHCH_3$ | 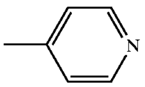 |

TABLE 1-continued
I
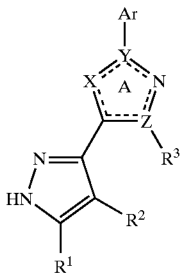
| No. | $R^3$ | $R^1$ | Ar |
|---|---|---|---|
| IA-21 | 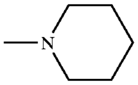 | $—CH_2NHCOCF_3$ | 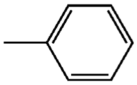 |
| IA-22 | 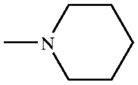 | $—CH_2N$-(cyclopropyl)$CO_2Me$ | 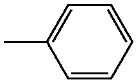 |
| IA-23 | 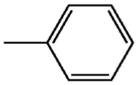 | $—CH_2NHCO_2—CH_2C{=}CH$ | 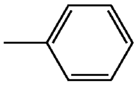 |
| IA-24 | 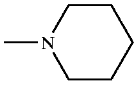 | $—CH_2NHCO_2—CH_2C{\equiv}CH$ | 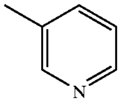 |
| IA-25 | 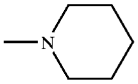 | $—CH_2NHCO_2—CH_2C{\equiv}CHCH_3$ | 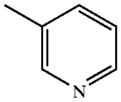 |
| IA-26 | 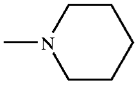 | $—CH_2NHCO_2CH_2C{\equiv}CCH_2N(Me)_2$ | 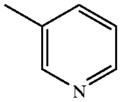 |
| IA-27 | 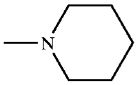 | $—CH_2NHCO_2C(Me)_2C{\equiv}CCH_2N(Me)_2$ | 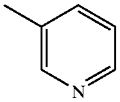 |
| IA-28 | 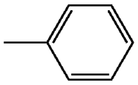 | $—CH_2NHCO_2Me$ | 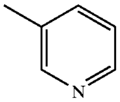 |
| IA-29 | 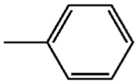 | $—CH_2NHCO_2Me$ | 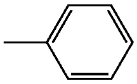 |
| IA-30 | 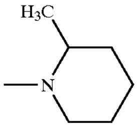 | $—CH_2NHCO_2Me$ | 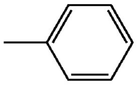 |
| IA-31 | 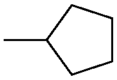 | $—CH_2NHCO_2Me$ | 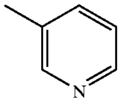 |

TABLE 1-continued
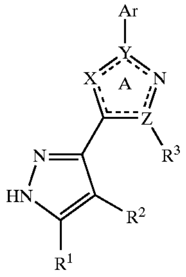
I
| No. | $R^3$ | $R^1$ | Ar |
| --- | --- | --- | --- |
| IA-32 | 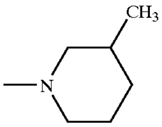 | $—CH_2NHCO_2Me$ | 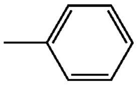 |
| IA-33 | 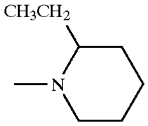 | $—CH_2NHCO_2Me$ | 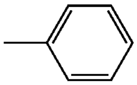 |
| IA-34 | $—N(Et)_2$ | $—CH_2NHCO_2Me$ | 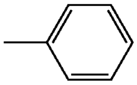 |
| IA-35 | 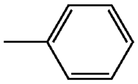 | $—CH_2NHCO_2Et$ | 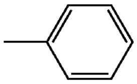 |
| IA-36 | 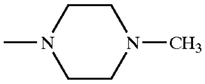 | $—CH_2NHCO_2Me$ | 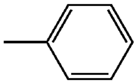 |
| IA-37 | 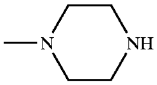 | $—CH_2NHCO_2Me$ | 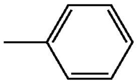 |
| IA-38 | 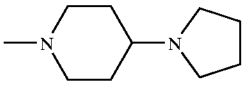 | $—CH_2NHCO_2Me$ | 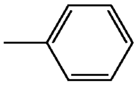 |
| IA-39 | 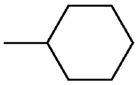 | $—CH_2NHCO_2—CH_2C≡CH$ | 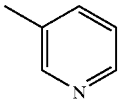 |
| IA-40 | 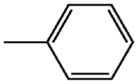 | $—CH_2NHCO_2—CH_2C≡CH$ | 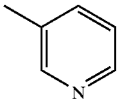 |
| IA-41 | 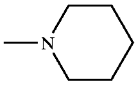 | $—CH_2NHCO_2—CH_2C≡CH$ | 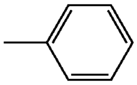 |
| IA-42 | 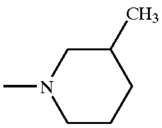 | $—CH_2NHCO_2—CH_2C≡CH$ | 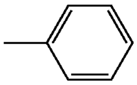 |

TABLE 1-continued
I
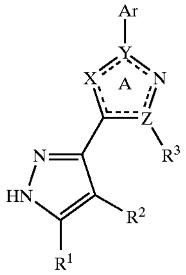
| No. | $R^3$ | $R^1$ | Ar |
| --- | --- | --- | --- |
| IA-43 | 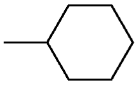 | $-CH_2NHCO_2Me$ | 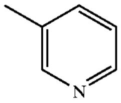 |
| IA-44 | 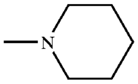 | $-CH_2NHCO_2-CH_2C\equiv CHCH_3$ | 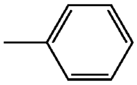 |
| IA-45 | 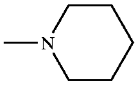 | $-CH_2NHCO_2-CH_2C\equiv CHCH_3$ | 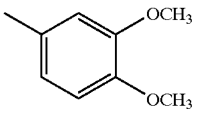 |
| IA-46 | 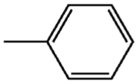 | $-CH_2NHCO_2-CH(CH_3)_2$ | 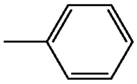 |
| IA-47 | 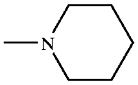 | $-CH_2NHCO_2-CH(CH_3)C\equiv CH$ | 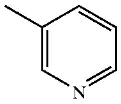 |
| IA-48 | 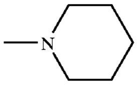 | $-CH_2NHCO_2-CH(CH_3)C\equiv CHCH_3$ | 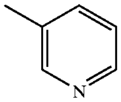 |
| IA-49 | 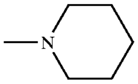 | $-CH_2NHCO_2-C(CH_3)_2C\equiv CH$ | 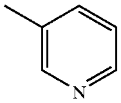 |
| IA-50 | 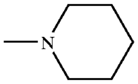 | $-CH_2NHCO_2-C(CH_3)_2C\equiv CHCH_3$ | 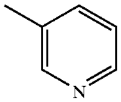 |
| IA-51 | 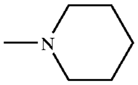 | 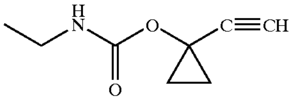 | 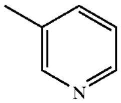 |
| IA-52 | 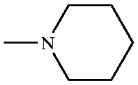 | 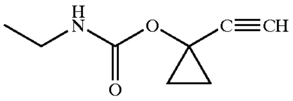 | 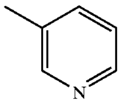 |
| IA-53 | 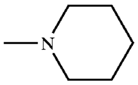 | 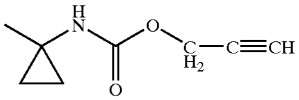 | 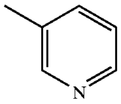 |

TABLE 1-continued
I
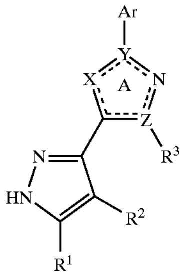
| No. | $R^3$ | $R^1$ | Ar |
|---|---|---|---|
| IA-54 | 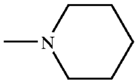 | 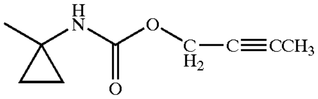 | 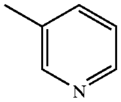 |
| IA-55 | 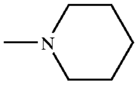 | $—C(CH_3)_2NHCO_2CH_2C{\equiv}CH$ | 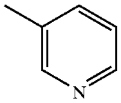 |
| IA-56 | 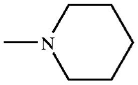 | $—C(CH_3)_2NHCO_2CH_2C{\equiv}CH$ | 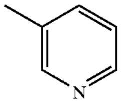 |
| IA-57 | 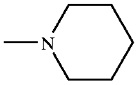 | $—C(CH_3)_2NHCO_2CH_2C{\equiv}CH$ | 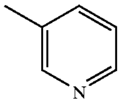 |
| IA-58 | 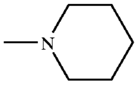 | $—C(CH_3)_2NHCO_2CH_2C{\equiv}CH$ | 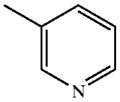 |
| IA-59 | 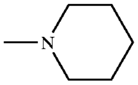 | $—CH(CH_3)NHCO_2CH_2C{\equiv}CHCH_3$ | 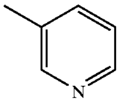 |
| IA-60 | 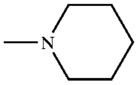 | $—CH(Et)NHCO_2CH_2C{\equiv}CHCH_3$ | 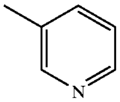 |
| IA-61 | 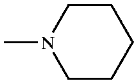 | $—CONH—OCH_2C{\equiv}CH$ | 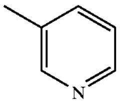 |
| IA-62 | 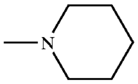 | $—CONH—OCH_2C{\equiv}CHCH_3$ | 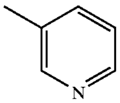 |
| IA-63 | 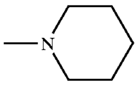 | $—CH_2NHCO_2CH_2C{\equiv}CCH_2N(Et)_2$ | 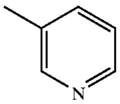 |

TABLE 1-continued
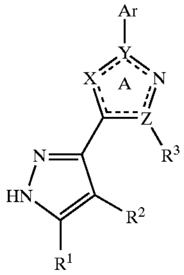
I
| No. | R³ | R¹ | Ar |
| --- | --- | --- | --- |
| IA-64 | 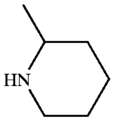 | $—CH_2NHCO_2—CH_2C{\equiv}CHCH_3$ | 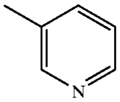 |
| IA-65 | 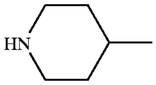 | $—CH_2NHCO_2—CH_2C{\equiv}CHCH_3$ | 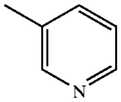 |
| IA-66 | 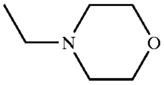 | $—CO_2Et$ | 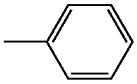 |
| IA-67 | 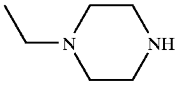 | $—CO_2Et$ | 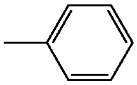 |
| IA-68 | 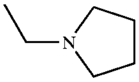 | $—CO_2Et$ | 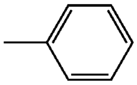 |
| IA-69 | 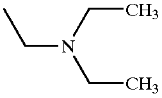 | $—CO_2Et$ | 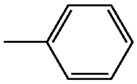 |
| IA-70 | 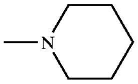 | $—CH(Pr)NHCO_2CH_2C{\equiv}CHCH_3$ | 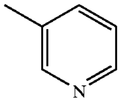 |
| IB-1 | 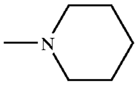 | $—CH_2NHCO_2Me$ | 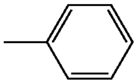 |
| IB-2 | 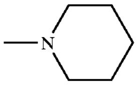 | $—CH_2NHCO_2Me$ | 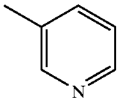 |
| IB-3 | 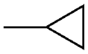 | $—CH_2NHCO_2—CH_2C{\equiv}CH$ | 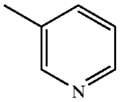 |
| IB-4 | 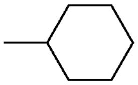 | $—CH_2NHCO_2—CH_2C{\equiv}CH$ | 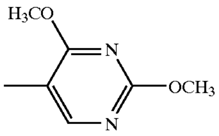 |

TABLE 1-continued
I
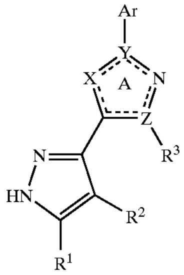
| No. | $R^3$ | $R^1$ | Ar |
|---|---|---|---|
| IB-5 | 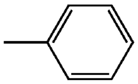 | $—CH_2NHCO_2—CH_2C{\equiv}CHCH_3$ | 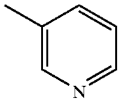 |
| IB-6 | 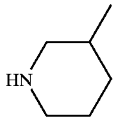 | $—CH_2NHCO_2—CH_2C{\equiv}CHCH_3$ | 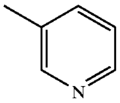 |
| IB-7 | 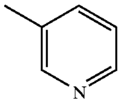 | $—CH_2NHCO_2—CH_2C{\equiv}CHCH_3$ | 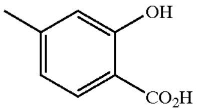 |
| IB-8 | 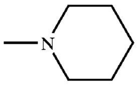 | —CONHEt | 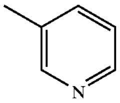 |
| IB-9 | 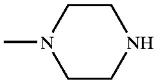 | $—CH_2NHCO_2Me$ | 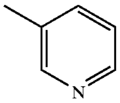 |
| IB-10 | $—(CH_2)_3CH_3$ | $—CH_2NHCO_2—CH_2C{\equiv}CH$ | 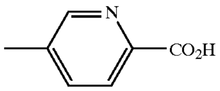 |
| IB-11 | 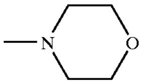 | $—CH_2NHCO_2—CH_2C{\equiv}CHCH_3$ | 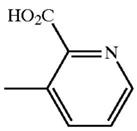 |
| IB-12 | $CH_2NHEt$ | $—CH_2NHCO_2—CH_2C{\equiv}CH$ | 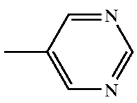 |
| IB-13 | $—N(Et)_2$ | $—CH_2NHCO_2—CH_2C{\equiv}CHCH_3$ | 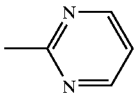 |
| IB-14 | 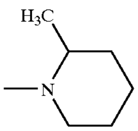 | $—CH_2NHCO_2—CH_2C{\equiv}CH$ | 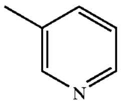 |

TABLE 1-continued
I
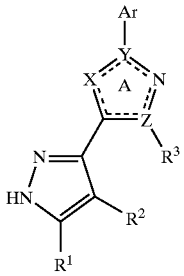
| No. | $R^3$ | $R^1$ | Ar |
|---|---|---|---|
| IB-15 | 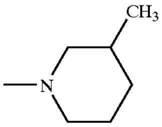 | $—CH_2NHCO_2—CH_2C{\equiv}CH$ | 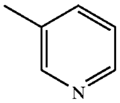 |
| IB-16 | 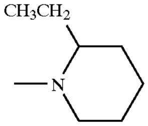 | $—CH_2NHCO_2—CH_2C{\equiv}CH$ | 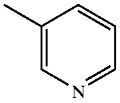 |
| IB-17 | 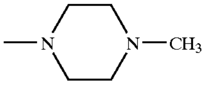 | $—CH_2NHCO_2—CH_2C{\equiv}CH$ | 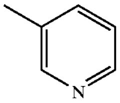 |
| IB-18 | 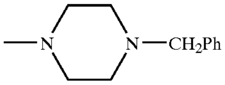 | $—CH_2NHCO_2Me$ | 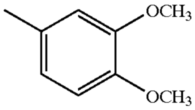 |
| IB-19 | $—CH_3$ | $—CH_2NHCO_2—CH_2C{\equiv}CHCH_3$ | 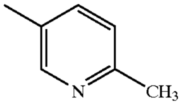 |
| IB-20 | $—CH_2OMe$ | $—CH_2NHCO_2—CH_2C{\equiv}CHCH_3$ | 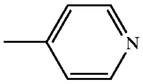 |
| IB-21 | 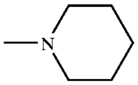 | $—CH_2NHCOCF_3$ | 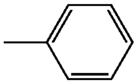 |
| IB-22 | 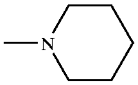 | $—CH_2N$-(cyclopropyl)$CO_2Me$ | 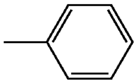 |
| IB-23 | 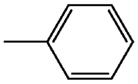 | $—CH_2NHCO_2—CH_2C{=}CH$ | 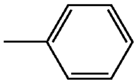 |
| IB-24 | 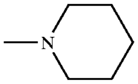 | $—CH_2NCO_2—CH_2C{\equiv}CH$ | 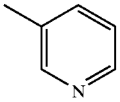 |

TABLE 1-continued
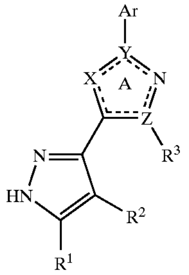
I
| No. | $R^3$ | $R^1$ | Ar |
|---|---|---|---|
| IB-25 | 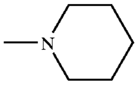 | $—CH_2NHCO_2—CH_2C{\equiv}CHCH_3$ | 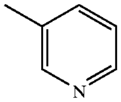 |
| IB-26 | 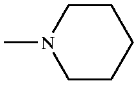 | $—CH_2NHCO_2CH_2C{\equiv}CCH_2N(Me)_2$ | 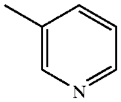 |
| IB-27 | 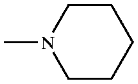 | $—CH_2NHCO_2C(Me)_2C{\equiv}CCH_2N(Me)_2$ | 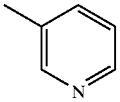 |
| IB-28 | 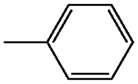 | $—CH_2NHCO_2—CH_2C{\equiv}CHCH_3$ | 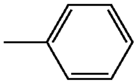 |
| IB-29 | $—CH_3$ | $—CH_2NHCO_2—CH_2C{\equiv}CHCH_3$ | 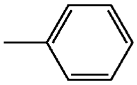 |
| IB-30 | 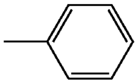 | $—CH_2NHCO_2Me$ | 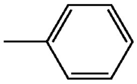 |
| IB-31 | $—CH_3$ | $—CH_2NHCO_2Me$ | 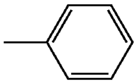 |
| IC-1 | 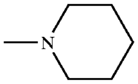 | $—CH_2NHCO_2Me$ | 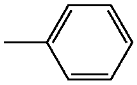 |
| IC-2 | 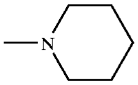 | $—CH_2NHCO_2Me$ | 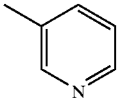 |
| IC-3 | 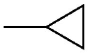 | $—CH_2NHCO_2—CH_2C{\equiv}CH$ | 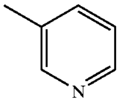 |
| IC-4 | 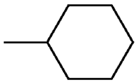 | $—CH_2NHCO_2—CH_2C{\equiv}CH$ | 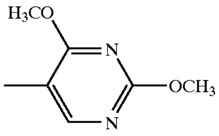 |

TABLE 1-continued
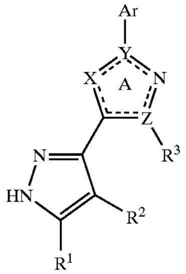
I
| No. | $R^3$ | $R^1$ | Ar |
|---|---|---|---|
| IC-5 | 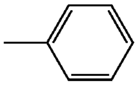 | $-CH_2NHCO_2-CH_2C\equiv CHCH_3$ | 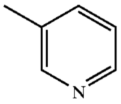 |
| IC-6 | 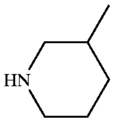 | $-CH_2NHCO_2-CH_2C\equiv CHCH_3$ | 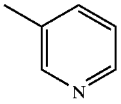 |
| IC-7 | 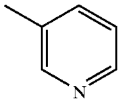 | $-CH_2NHCO_2-CH_2C\equiv CHCH_3$ | 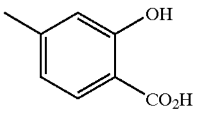 |
| IC-8 | 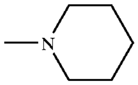 | —CONHEt | 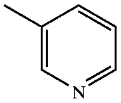 |
| IC-9 | 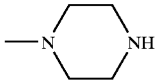 | $-CH_2NHCO_2Me$ | 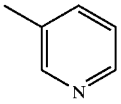 |
| IC-10 | $-(CH_2)_3CH_3$ | $-CH_2NHCO_2-CH_2C\equiv CH$ | 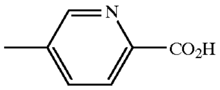 |
| IC-11 | 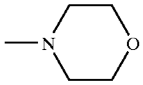 | $-CH_2NHCO_2-CH_2C\equiv CHCH_3$ | 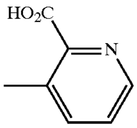 |
| IC-12 | $-CH_2NHEt$ | $-CH_2NHCO_2-CH_2C\equiv CH$ | 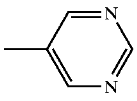 |
| IC-13 | $-N(Et)_2$ | $-CH_2NHCO_2-CH_2C\equiv CHCH_3$ | 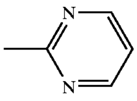 |
| IC-14 | 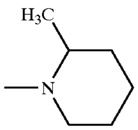 | $-CH_2NHCO_2-CH_2C\equiv CH$ | 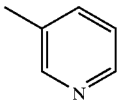 |

TABLE 1-continued
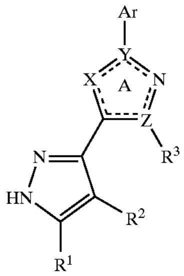
I
| No. | $R^3$ | $R^1$ | Ar |
|---|---|---|---|
| IC-15 | 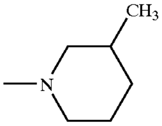 | $-CH_2NHCO_2-CH_2C\equiv CH$ | 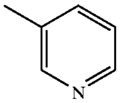 |
| IC-16 | 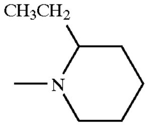 | $-CH_2NHCO_2-CH_2C\equiv CH$ | 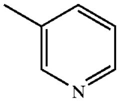 |
| IC-17 | 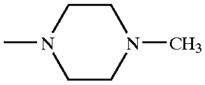 | $-CH_2NHCO_2-CH_2C\equiv CH$ | 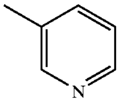 |
| IC-18 | 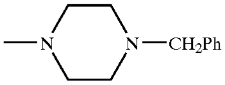 | $-CH_2NHCO_2Me$ | 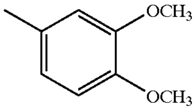 |
| IC-19 | $-CH_3$ | $-CH_2NHCO_2-CH_2C\equiv CHCH_3$ | 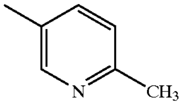 |
| IC-20 | $-CH_2OMe$ | $-CH_2NHCO_2-CH_2C\equiv CHCH_3$ | 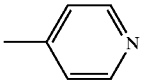 |
| IC-21 | 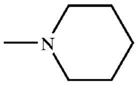 | $-CH_2NHCOCF_3$ | 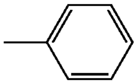 |
| IC-22 | 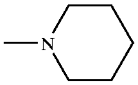 | $-CH_2N$-(cyclopropyl)$CO_2Me$ | 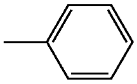 |
| IC-23 | 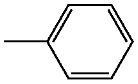 | $-CH_2NHCO_2-CH_2C=CH$ | 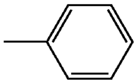 |
| IC-24 | 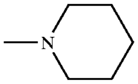 | $-CH_2NHCO_2-CH_2C\equiv CH$ | 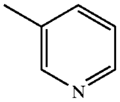 |

TABLE 1-continued
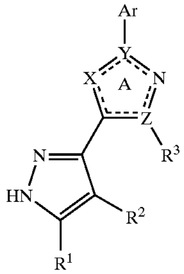
I
| No. | $R^3$ | $R^1$ | Ar |
|---|---|---|---|
| IC-25 | 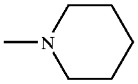 | $—CH_2NHCO_2—CH_2C{\equiv}CHCH_3$ | 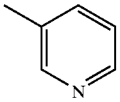 |
| IC-26 | 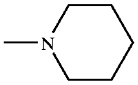 | $—CH_2NHCO_2CH_2C{\equiv}CCH_2N(Me)_2$ | 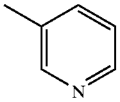 |
| IC-27 | 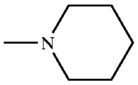 | $—CH_2NHCO_2C(Me)_2C{\equiv}CCH_2N(Me)_2$ | 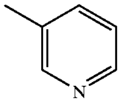 |
| ID-1 | 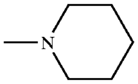 | $—CH_2NHCO_2Me$ | 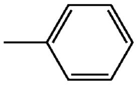 |
| ID-2 | 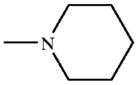 | $—CH_2NHCO_2Me$ | 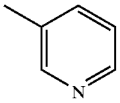 |
| ID-3 | 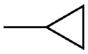 | $—CH_2NHCO_2—CH_2C{\equiv}CH$ | 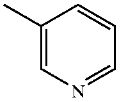 |
| ID-4 | 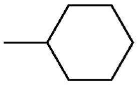 | $—CH_2NHCO_2—CH_2C{\equiv}CH$ | 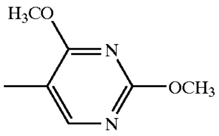 |
| ID-5 | 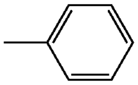 | $—CH_2NHCO_2—CH_2C{\equiv}CHCH_3$ | 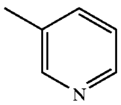 |
| ID-6 | 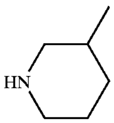 | $—CH_2NHCO_2—CH_2C{\equiv}CHCH_3$ | 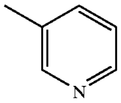 |
| ID-7 | 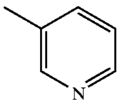 | $—CH_2NHCO_2—CH_2C{\equiv}CHCH_3$ | 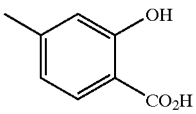 |

TABLE 1-continued
I
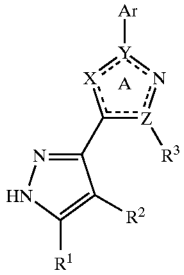
| No. | $R^3$ | $R^1$ | Ar |
|---|---|---|---|
| ID-8 | 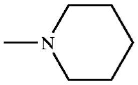 | —CONHEt | 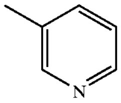 |
| ID-9 | 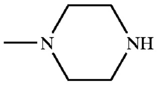 | —$CH_2NHCO_2Me$ | 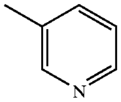 |
| ID-10 | —$(CH_2)_3CH_3$ | —$CH_2NHCO_2$—$CH_2C{\equiv}CH$ | 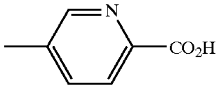 |
| ID-11 | 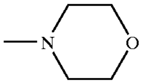 | —$CH_2NHCO_2$—$CH_2C{\equiv}CHCH_3$ | 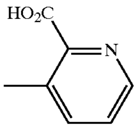 |
| ID-12 | —$CH_2NHEt$ | —$CH_2NHCO_2$—$CH_2C{\equiv}CH$ | 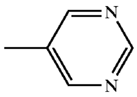 |
| ID-13 | —$N(Et)_2$ | —$CH_2NHCO_2$—$CH_2C{\equiv}CHCH_3$ | 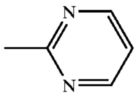 |
| ID-14 | 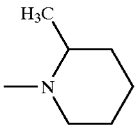 | —$CH_2NHCO_2$—$CH_2C{\equiv}CH$ | 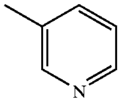 |
| ID-15 | 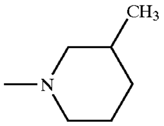 | —$CH_2NHCO_2$—$CH_2C{\equiv}CH$ | 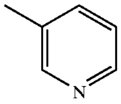 |
| ID-16 | 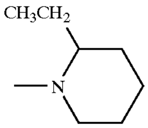 | —$CH_2NHCO_2$—$CH_2C{\equiv}CH$ | 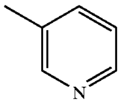 |
| ID-17 | 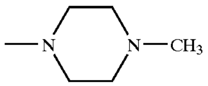 | —$CH_2NHCO_2$—$CH_2C{\equiv}CH$ | 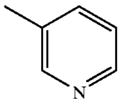 |

TABLE 1-continued
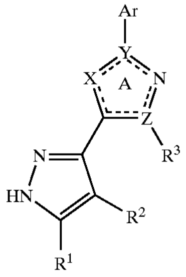
I
| No. | $R^3$ | $R^1$ | Ar |
|---|---|---|---|
| ID-18 | 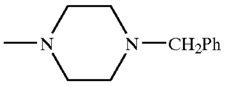 | $-CH_2NHCO_2Me$ | 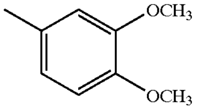 |
| ID-19 | $-CH_3$ | $-CH_2NHCO_2-CH_2C{\equiv}CHCH_3$ | 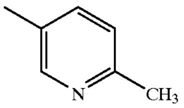 |
| ID-20 | $-CH_2OMe$ | $-CH_2NHCO_2-CH_2C{\equiv}CHCH_3$ | 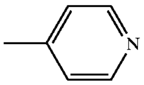 |
| ID-21 | 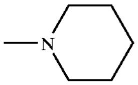 | $-CH_2NHCOCF_3$ | 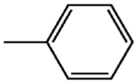 |
| ID-22 | 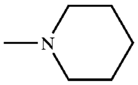 | $-CH_2N$-(cyclopropyl)$CO_2Me$ | 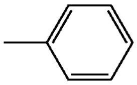 |
| ID-23 | 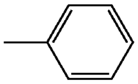 | $-CH_2NHCO_2-CH_2C{\equiv}CH$ | 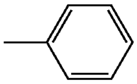 |
| ID-24 | 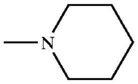 | $-CH_2NHCO_2-CH_2C{\equiv}CH$ | 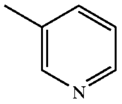 |
| ID-25 | 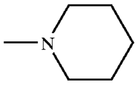 | $-CH_2NHCO_2-CH_2C{\equiv}CHCH_3$ | 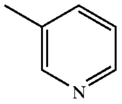 |
| ID-26 | 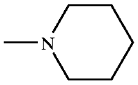 | $-CH_2NHCO_2CH_2C{\equiv}CCH_2N(Me)_2$ | 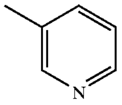 |
| ID-27 | 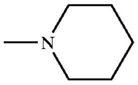 | $-CH_2NHCO_2C(Me)_2C{\equiv}CCH_2N(Me)_2$ | 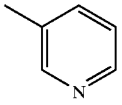 |
| IE-1 | 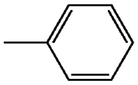 | $-CH_2NHCO_2Me$ | 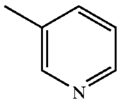 |

TABLE 1-continued
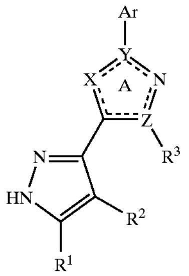
I
| No. | $R^3$ | $R^1$ | Ar |
|---|---|---|---|
| IE-2 | 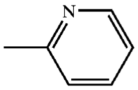 | $-CH_2NHCO_2Me$ | 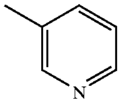 |
| IE-3 | 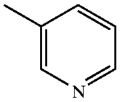 | $-CH_2NHCO_2Me$ | 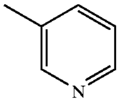 |
| IE-4 | 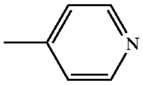 | $-CH_2NHCO_2Me$ | 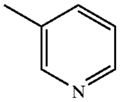 |
| IE-5 | 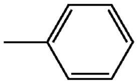 | $-CH_2NHCO_2-CH_2C\equiv CH$ | 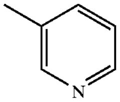 |
| IE-6 | 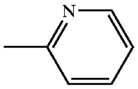 | $-CH_2NHCO_2-CH_2C\equiv CH$ | 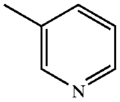 |
| IE-7 | 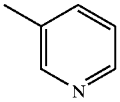 | $-CH_2NHCO_2-CH_2C\equiv CH$ | 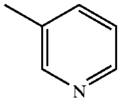 |
| IE-8 | 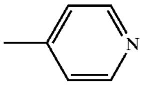 | $-CH_2NHCO_2-CH_2C\equiv CH$ | 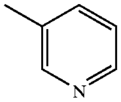 |
| IE-9 | 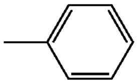 | $-CH_2NHCO_2-CH_2C\equiv CHCH_3$ | 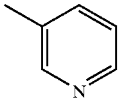 |
| IE-10 | 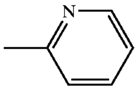 | $-CH_2NHCO_2-CH_2C\equiv CHCH_3$ | 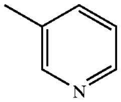 |
| IE-11 | 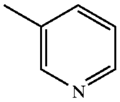 | $-CH_2NHCO_2-CH_2C\equiv CHCH_3$ | 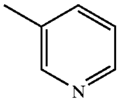 |

TABLE 1-continued
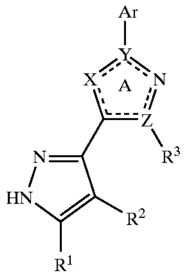
I
| No. | $R^3$ | $R^1$ | Ar |
| --- | --- | --- | --- |
| IE-12 | 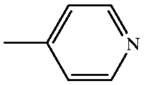 | $—CH_2NHCO_2—CH_2C{\equiv}CHCH_3$ | 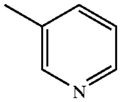 |
| IE-13 | 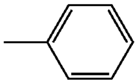 | $—CH_2NHCO_2CH_2C{\equiv}CCH_2N(Me)_2$ | 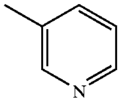 |
| IE-14 | 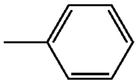 | $—CH_2NHCO_2C(Me)_2C{\equiv}CCH_2N(Me)_2$ | 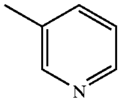 |
| IE-15 | 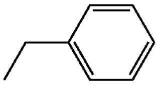 | $—CH_2NHCO_2—CH_2C{\equiv}CHCH_3$ | 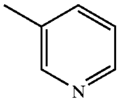 |
| IE-16 | 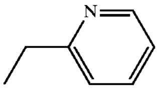 | $—CH_2NHCO_2—CH_2C{\equiv}CHCH_3$ | 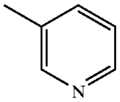 |
| IE-17 | 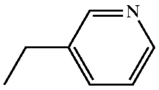 | $—CH_2NHCO_2—CH_2C{\equiv}CHCH_3$ | 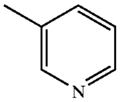 |
| IE-18 | 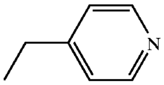 | $—CH_2NHCO_2—CH_2C{\equiv}CHCH_3$ | 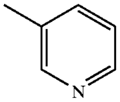 |
| IE-19 | 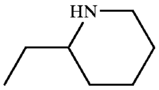 | $—CH_2NHCO_2—CH_2C{\equiv}CHCH_3$ | 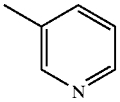 |
| IE-20 | 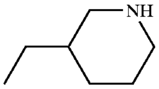 | $—CH_2NHCO_2—CH_2C{\equiv}CHCH_3$ | 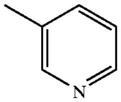 |
| IE-21 | 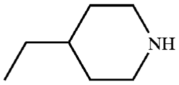 | $—CH_2NHCO_2—CH_2C{\equiv}CHCH_3$ | 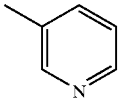 |

TABLE 1-continued

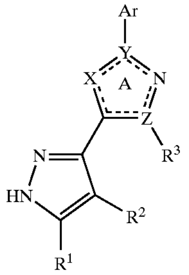

I

| No. | $R^3$ | $R^1$ | Ar |
| --- | --- | --- | --- |
| IE-22 | Et | $-CH_2NHCO_2CH_3$ | 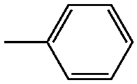 |
| IE-23 | Et | $-CH_2NHCO_2-CH_2C{\equiv}CHCH_3$ | 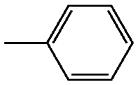 |

The compounds of this invention may be prepared in general by methods known to those skilled in the art for analogous compounds and by referring to the synthetic schemes shown below. A general reference is Katritzky and Rees, *Comprehensive Heterocyclic Chemistry*, vol. 5, 1984, Pergamon Press. In the routes shown below, the Ar group of formula I may be represented by a phenyl ring. It will be apparent to one skilled in the art that these routes are generally applicable to compounds having aryl groups other than phenyl.

Scheme I

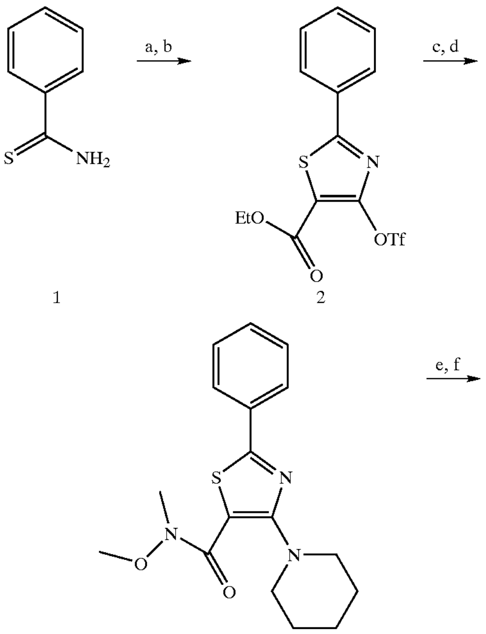

1 2 3

-continued

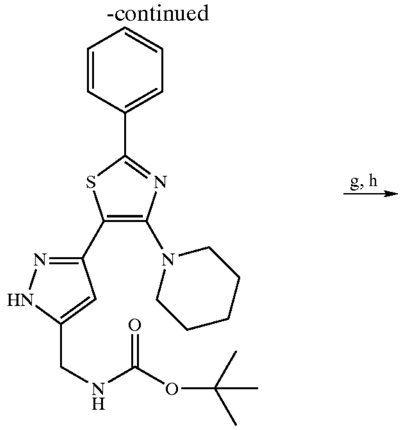

4

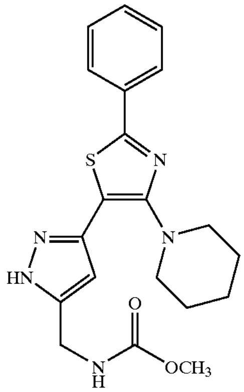

5

Reagents and conditions: (a) $(EtO_2C)_2CHBr$, pyridine, toluene, heat (b) triflic anhydride, 2,6-lutidine, $CH_2Cl_2$, 0° C. (c) $Me_2AlCl$, MeNHOMe·HCl, $CH_2Cl_2$, 0° C. (d) piperidine, toluene, heat (e) $LiC{\equiv}CCH_2N(Li)CO_2t$-Bu, THF, 0° C.→RT (f) $H_2NNH_2$, EtOH, RT (g) trifluoroacetic acid, $CH_2Cl_2$ (h) imidazole-1-carboxylic acid methyl ester, acetonitrile, heat.

Scheme I above shows a route for the preparation of thiazole compounds of this invention where the 4-position ($R^3$) of the thiazole ring is substituted by an amino group, illustrated here where Ar is phenyl and $R^3$ is piperidine. It will be apparent to one skilled in the art that the piperidine reactant in step (d) may be replaced by other amines to provide other 4-(amino group-substituted)thiazoles.

Scheme II

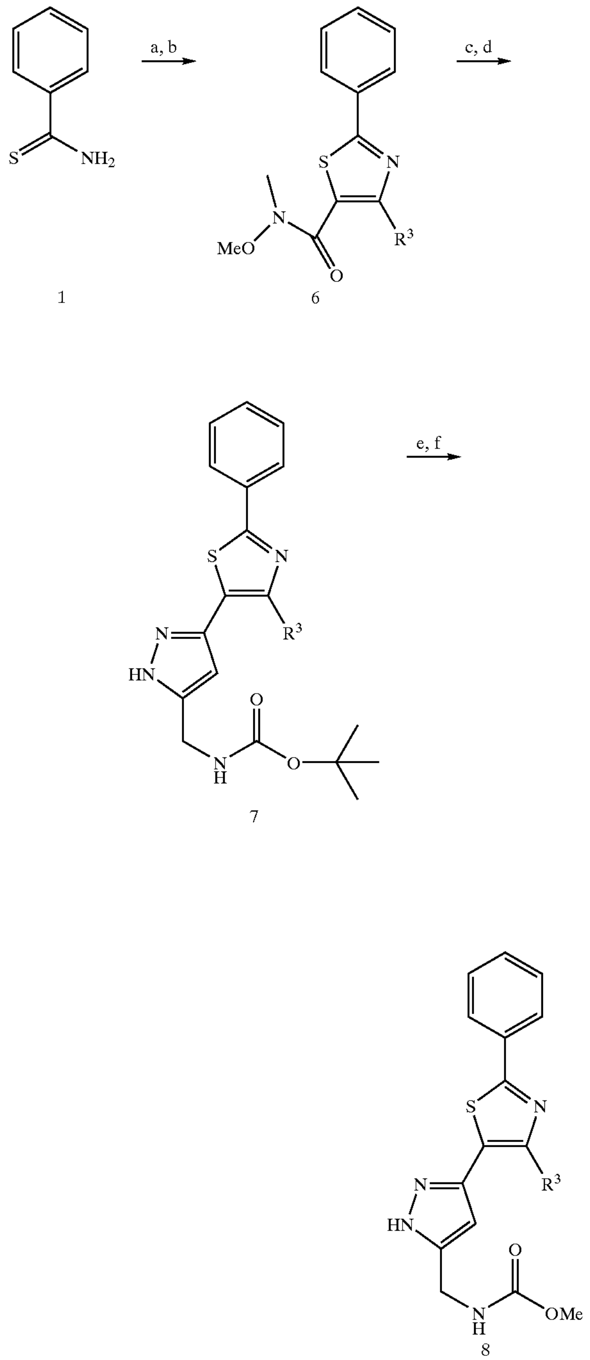

1 6 7 8

Reagents and conditions: (a) $EtO_2CCH(Cl)C(=O)R^3$, EtOH, heat (b) $Me_2AlCl$, MeNHOMe·HCl, $CH_2Cl_2$, 0° C. (c) $LiC{\equiv}CCH_2N(Li)CO_2t\text{-}Bu$, THF, 0° C.→RT (d) $H_2NNH_2$, EtOH, RT (e) trifluoroacetic acid, $CH_2Cl_2$ (f) imidazole-1-carboxylic acid methyl ester, acetonitrile, heat.

Scheme II above shows a general route to thiazole compounds of formula IA wherein $R^3$ is an alkyl or aryl group.

Scheme III

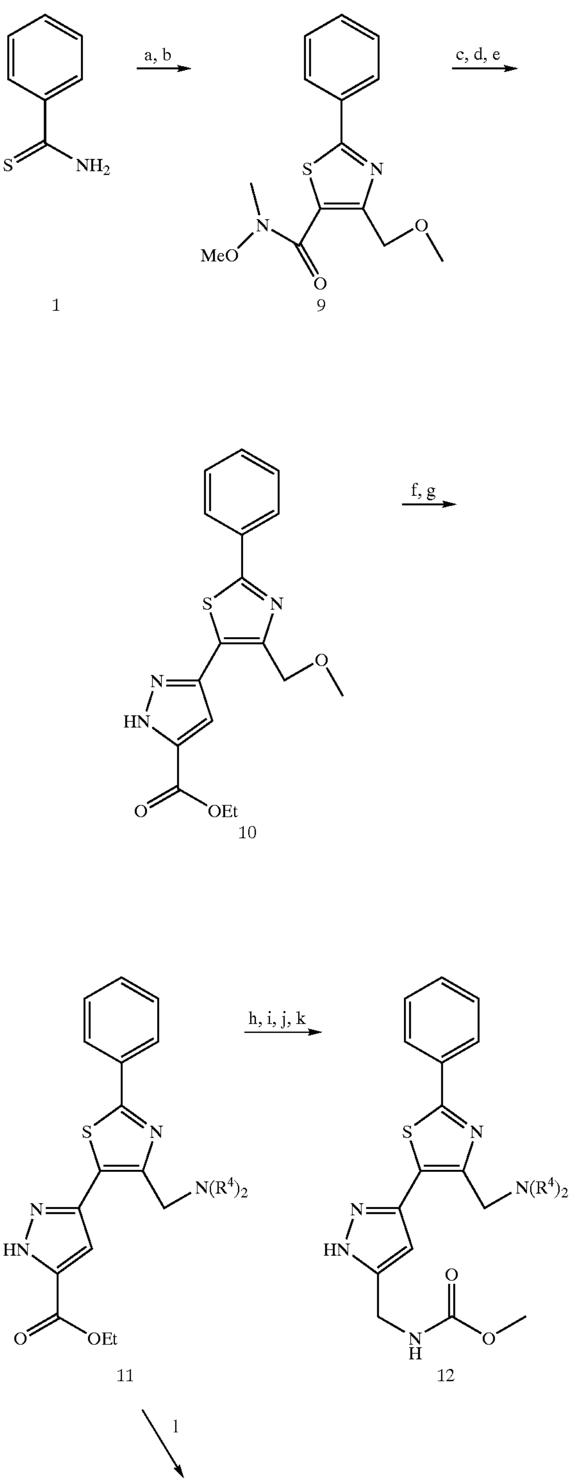

1 9 10 11 12

-continued

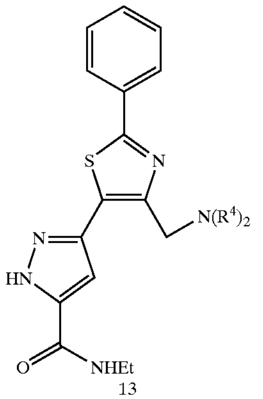

13

Reagents and conditions: (a) $EtO_2CCH(Cl)COCH_2OCH_3$, EtOH, heat (b) $Me_2AlCl$, MeNHOMe·HCl, $CH_2Cl_2$, 0° C. (c) MeMgBr, THF, 0° C. (d) KOtBu, diethyl oxalate, THF, RT (e) $H_2NNH_2$, acetic acid, EtOH (f) $BBr_3$, $CH_2Cl_2$ (g) $(R^4)_2NH$, THF (h) $LiAlH_4$, THF (i) $SOCl_2$, $CH_2Cl_2$, 0° C. (j) $NH_3$, dioxane (k) imidazole-1-carboxylic acid methyl ester, acetonitrile, heat (l) $EtNH_2$, MeOH, heat.

Scheme III above shows a general route to compounds of formula IA where $R^3$ is $(CH_2)_pN(R^4)_2$ and p is one.

Scheme IV

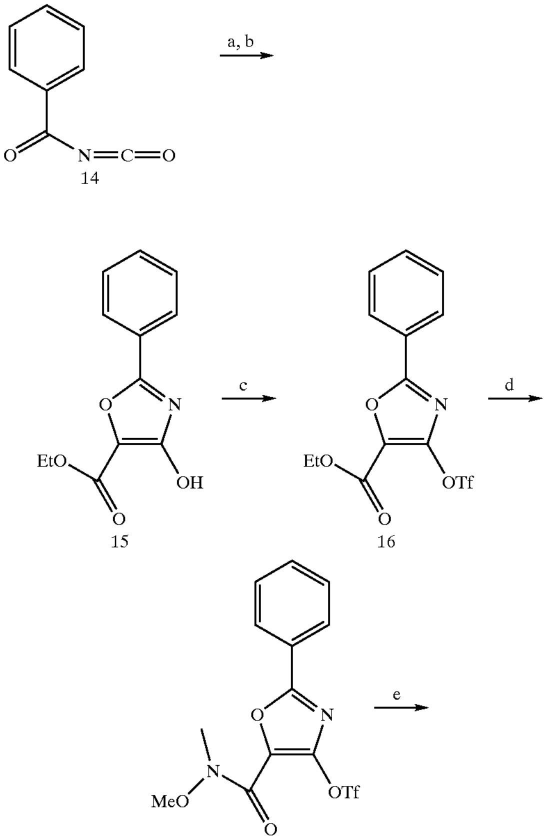

14

15

16

17

-continued

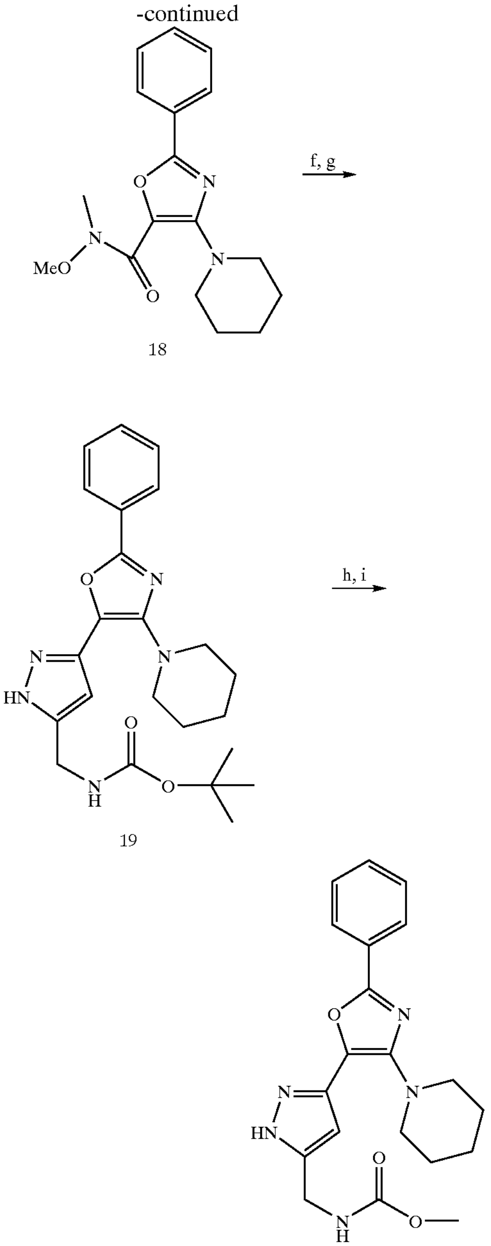

18

19

20

Reagents and conditions: (a) $EtO_2CCHS^+(Me)_2Br^-$, 60% NaH, THF (b) decalin, 195° C. (c) triflic anhydride, 2,6-lutidine, $CH_2Cl_2$, 0° C. (d) $Me_2AlCl$, MeNHOMe.HCl, $CH_2Cl_2$, 0° C.→RT (e) piperidine, toluene, 90° C. (f) $CH{\equiv}CCH_2NHCO_2tBu$, n-BuLi, −15° C.→10° C. (g) $H_2NNH_2·H_2O$, EtOH, RT (h) (4:1) $CH_2Cl_2$-TFA (i) $ClCO_2Me$, EtOAc, 1.0N $NaHCO_3$ Scheme IV above shows a route for the preparation of oxazole compounds IB of this invention where the 4-position ($R^3$) of the oxazole ring is substituted by an amino group, illustrated here where Ar is phenyl and $R^3$ is piperidine. The formation of the oxazolone ring according to steps (a) and (b) is based on the method reported in *Tetrahedron*, Vol.29, 1983–1990 (1973).

Scheme V

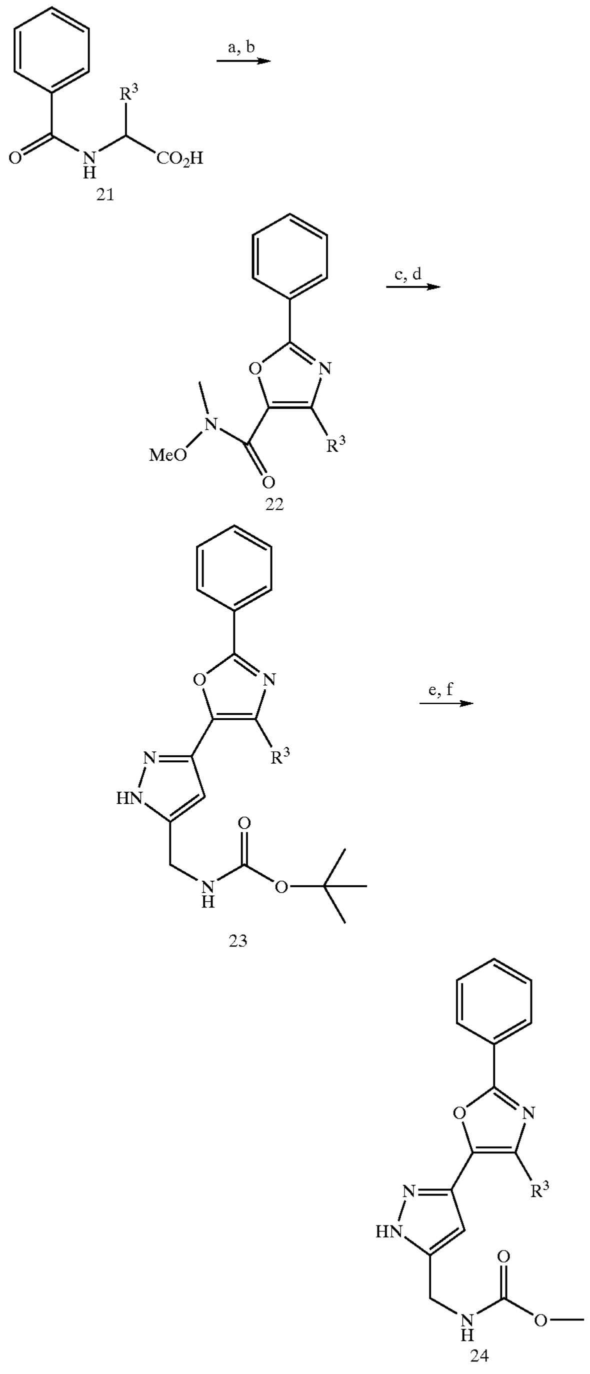

21

22

23

24

Reagents and conditions: (a) $(COCl)_2$, benzene, $CH_2Cl_2$, RT (b) MeNHOMe·HCl, $Et_3N$, 0° C.→RT (c) piperidine, toluene, 90° C. (d) CH≡$CCH_2NHCO_2tBu$, n-BuLi, −15° C.→10° C. (e) $H_2NNH_2 \cdot H_2O$, EtOH, RT (f) (4:1) $CH_2Cl_2$-TFA (i) $ClCO_2Me$, EtOAc, 1.0N $NaHCO_3$ Scheme V above shows a route for the preparation of oxazoles IB where the 4-position of the oxazole ring ($R^3$) is substituted by various groups, for example, an aliphatic group. The formation of the oxazole ring according to step (a) is based on the method reported in J. Chem. Soc., Chem. Commun., 29–30 (1995).

Scheme VI

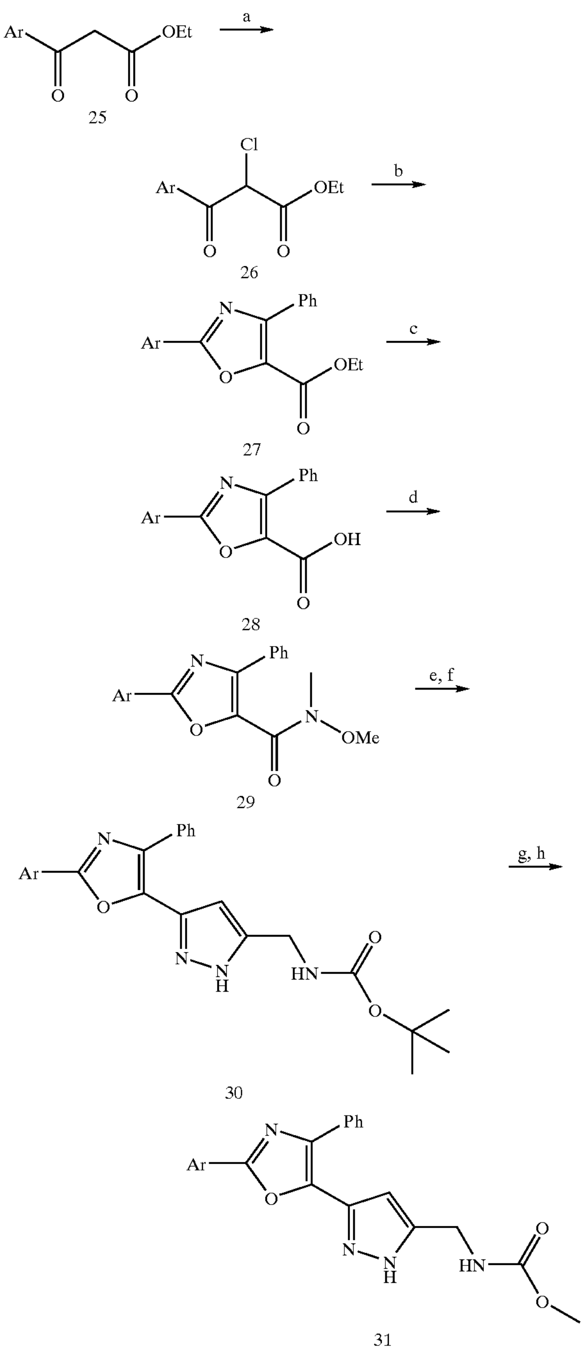

25

26

27

28

29

30

31

Reagents and conditions: (a) $ClSO_2Cl$, $CH_2Cl_2$, RT (b) $PhCONH_2$, neat, 150° C. (c) 2N NaOH, dioxane (d) i. carbonyldiimidazole, THF; ii. MeNHOMe·HCl, $Et_3N$ (e) CH≡$CCH_2NHCO_2tBu$, n-BuLi, −15° C.→10° C. (f) $H_2NNH_2 \cdot H_2O$, EtOH, RT (g) (4:1) $CH_2Cl_2$-TFA (h) $ClCO_2Me$, EtOAc, 1.0N $NaHCO_3$ Scheme VI above shows a route for the preparation of IB compounds where the 4-position of the oxazole ring ($R^3$) is substituted by an aryl group, as illustrated here using a phenyl group.

Scheme VII

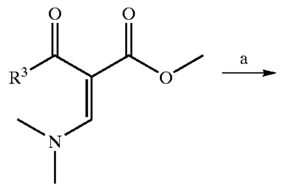

37

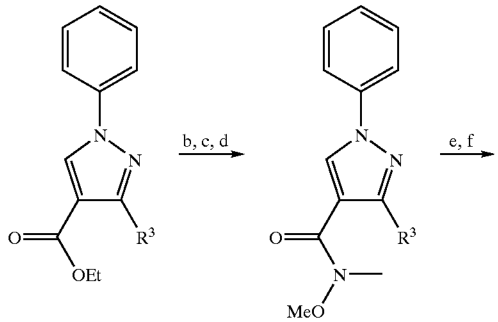

38 39

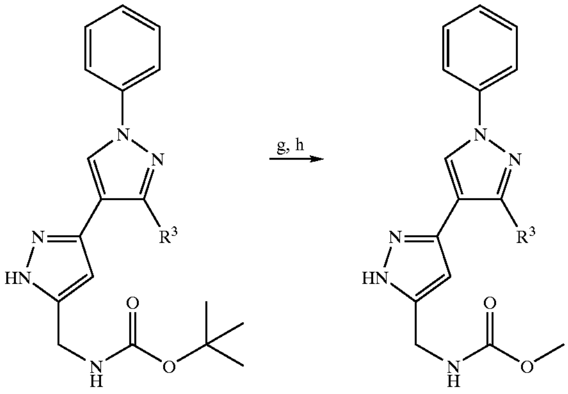

40 41

Reagents and conditions: (a) $PhNHNH_2$, $Et_2O$, RT (b) aq. NaOH, MeOH (c) carbonyldiimidazole, THF (d) MeNHOMe·HCl, diisopropylethylamine, DMF, 80° C. (e) $LiC{\equiv}CCH_2N(Li)CO_2tBu$, THF, 0° C.→RT (f) $H_2NNH_2$, EtOH, RT (g) $CH_2Cl_2$, TFA (h) 1-imidazolecarboxylic acid methyl ester, acetonitrile, heat Scheme VII above shows a general route to formula ID pyrazoles. This route is particularly suitable for compounds where the $R^3$ substituent is aliphatic or aryl.

Scheme VIII

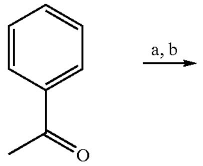

32

-continued

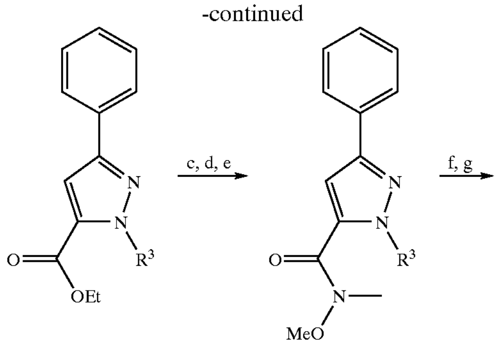

33 34

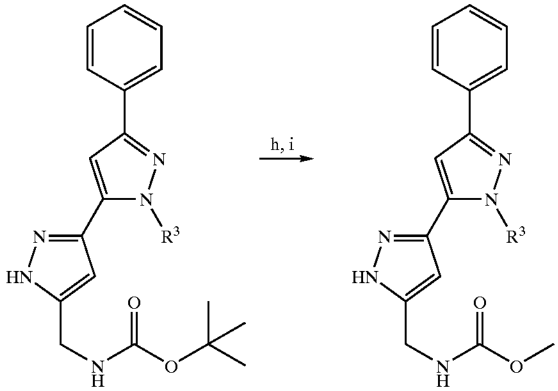

35 36

Reagents and conditions: (a) KOtBu, diethyloxalate, THF, RT (b) (i) $H_2NNHR$, —HOAc, EtOH (ii) separate (c) aq. NaOH, MeOH (d) carbonyldiimidazole, THF (e) MeNHOMe·HCl, diisopropylethylamine, DMF, 80° C. (f) $LiC{\equiv}CCH_2N(Li)CO_2tBu$, THF, 0° C.→RT (g) $H_2NNH_2$, EtOH, RT (h) $CH_2Cl_2$, TFA (i) 1-imidazolecarboxylic acid methyl ester, acetonitrile, heat Scheme VIII above shows a general route for the preparation of formula IE pyrazoles.

The pharmaceutical compositions and methods of this invention will be useful generally for controlling bacterial infections in vivo. Examples of bacterial organisms that may be controlled by the compositions and methods of this invention include, but are not limited to the following organisms: *Streptococcus pneumoniae, Streptococcus pyogenes, Enterococcus fecalis, Enterococcus faecium, Klebsiella pneumoniae, Enterobacter* sps., *Proteus* sps., *Pseudomonas aeruginosa, E. coli, Serratia marcesens, S. aureus*, Coag. Neg. Staph., *Acinetobacter* sps., *Salmonella* sps, *Shigella* sps., *Helicobacter pylori, Mycobacterium tuberculosis, Mycobacterium avium, Mycobacterium intracellulare, Mycobacterium fortuitum, Mycobacterium chelonae, Mycobacterium kansasii, Haemophilus influenzae, Stenotrophomonas maltophilia*, and *Streptococcus agalactiae*. The compositions and methods will therefore be useful for controlling, treating or reducing the advancement, severity or effects of nosocomial or non-nosocomial infections. Examples of nosocomial infection uses include, but are not limited to, urinary tract infections, pneumonia, surgical wound infections, bone and joint infections, and bloodstream infections. Examples of non-nosocomial uses include but are not limited to urinary tract infections, pneumonia, prostatitis, skin and soft tissue infections, bone and joint infections, intra-abdominal infections, meningitis, brain abscess, infectious diarrhea and gastrointestinal infections, surgical prophylaxis, and therapy for febrile neutropenic patients. The term "non-nosocomial infections" is also referred to as community acquired infections.

Pharmaceutical compositions of this invention comprise a compound of formula I or a pharmaceutically acceptable salt thereof and a pharmaceutically acceptable carrier. Such compositions may optionally comprise an additional therapeutic agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

In pharmaceutical composition comprising only a compound of formula I as the active component, methods for administering these compositions may additionally comprise the step of administering to the subject an additional agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

The compounds of formula I may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The pharmaceutical compositions of this invention may be administered orally, parenterally, by inhalation spray, topically, via ophthalmic solution or ointment, rectally, nasally, buccally, vaginally or via an implanted reservoir. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus fecalis, Enterococcus faecium, Klebsiella pneumoniae, Enterobacter* sps. *Proteus* sps. *Pseudomonas aeruginosa, E. coli, Serratia marcesens, S. aureus*, and Coag. Neg. Staph.

Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage, dosage form, or frequency of administration, or both, may need to be modified. In some cases, patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

One embodiment of this invention provides a method for treating or preventing a bacterial infection or disease in a subject comprising the step of administering to the subject any compound, pharmaceutical composition, or combination described herein and a pharmaceutically acceptable carrier.

The compounds of this invention are also useful as commercial reagents which effectively bind to the gyrase B enzyme. As commercial reagents, the compounds of this invention, and their derivatives, may be used to block gyrase B activity in biochemical or cellular assays for bacterial gyrase B or its homologs or may be derivatized to bind to a stable resin as a tethered substrate for affinity chromatography applications. These and other uses which characterize commercial gyrase B inhibitors will be evident to those of ordinary skill in the art.

In order that this invention be more fully understood, the following examples are set forth. These examples are for the purpose of illustration only and are not to be construed as limiting the scope of the invention in any way.

SYNTHETIC EXAMPLES

Example 1

2-Phenyl-4-trifluoromethanesulfonyloxy-thiazole-5-carboxylic acid ethyl ester

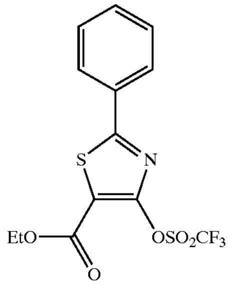

The starting material 4-hydroxy-2-phenyl-thiazole-5-carboxylic acid ethyl ester was prepared according to the procedure described by Kedersky et al., *J. Med. Chem.*, 34, 2158 (1991). To a solution of the starting material (2.3 mmol) in $CH_2Cl_2$ (10 mL) at 0° C. was successively added 2,6-lutidine (2.53 mmol) and trifluoromethanesulfonic anhydride (2.53 mmol). The reaction was stirred from 0° C. to room temperature over a two hours period. The reaction mixture was diluted with $CH_2Cl_2$ and washed successively with 5% $NaHSO_4$, water, $NaHCO_3$, and saturated brine, then dried over $MgSO_4$ and concentrated in vacuo. Silica gel chromatography of the crude material provided 82% of the desired product the title compound as a white crystalline solid with consistent $^1H$ NMR ($CDCl_3$): δ 1.4 (t, 3H), 4.4 (q, 2H), 7.4–7.6 (m, 3H), 7.95 (m, 2H).

Example 2

2-Phenyl-4-piperidin-1-yl-thiazole-5-carboxylic acid ethyl ester

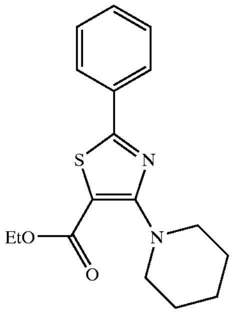

To a solution of the above-prepared 2-phenyl-4-trifluoromethanesulfonyloxy-thiazole-5-carboxylic acid ethyl ester (0.75 mmol) in toluene (5 mL) was added piperidine (4.5 mmol). The reaction mixture was heated to 80° C. for 2 hours. The mixture was then diluted in ethyl acetate, washed successively with water and brine, and dried over $MgSO_4$. Silica gel chromatography of the crude mixture provided title compound (96%) as a yellowish oil.

Example 3

2-Phenyl-4-piperidin-1-yl-thiazole-5-carboxylic acid methoxy-methyl-amide

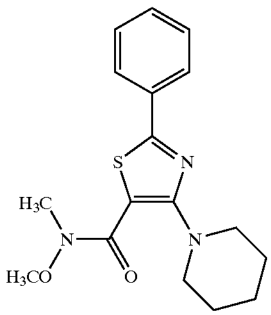

A solution of N,O-dimethylhydroxylamine hydrochloride (3.62 mmol) in dry $CH_2Cl_2$ (5 ml) at 0° C. was treated dropwise with neat dimethylaluminum chloride (3.62 mmol) and the resulting mixture stirred at 0° C. for 0.5 hours. The mixture was then allowed to warm to room temperature before adding the above-prepared 2-phenyl-4-piperidin-1-yl-thiazole-5-carboxylic acid ethyl ester (0.724 mmol) in $CH_2Cl_2$ (2 ml) dropwise. The yellow mixture was then stirred at room temperature under nitrogen for one hour and re-cooled to 0° C. The mixture was quenched slowly by adding 2.0N NaOH dropwise, warmed to room temperature, and extracted with two portions of $CH_2Cl_2$. The organic phase was washed successively with 1.0N NaOH and brine, dried over $MgSO_4$, and concentrated in vacuo to give a yellow oil. Silica gel chromatography provided 3 as a yellow waxy crystalline solid (98% yield). $^1H$ NMR ($CDCl_3$): δ 3.35 (s, 3H), 1.6–1.8 (m, 6H), 3.3 (s, 3H), 3.5 (m, 4H), 3.7 (s, 3H), 7.3–7.4 (m, 3H), 7.95 (m, 2H).

Example 4

1-(2-Phenyl-4-piperidin-1-yl-thiazol-5-yl)-ethanone

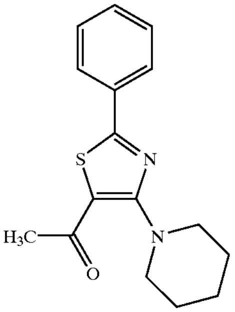

To a solution of the above-prepared 2-phenyl-4-piperidin-1-yl-thiazole-5-carboxylic acid methoxy-methyl-amide (0.754 mmol) in THF (5 mL) was added at 0° C. MeLi.LiBr (0.83 mmol). The reaction mixture was stirred until the reaction was complete, then quenched by the addition of saturated ammonium chloride and extracted with ethyl acetate. The organic phase was washed with brine, dried over $MgSO_4$ and concentrated in vacuo to give a brown oil. Silica gel chromatography provided the title compound (72%) as a yellowish oil. $^1H$ NMR ($CDCl_3$): δ 1.6–1.8 (m, 6H), 2.45 (s, 3H), 3.5 (m, 4H), 7.4–7.5 (m, 3H), 8.0 (m, 2H).

Example 5

5-(2-Phenyl-4-piperidin-1-yl-thiazol-5-yl)-2H-pyrazole-3-carboxylic acid ethyl ester

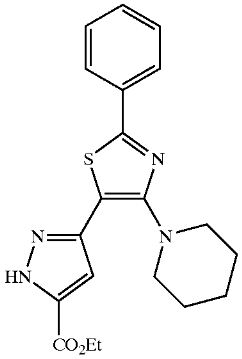

To a solution of the above-prepared 1-(2-phenyl-4-piperidin-1-yl-thiazol-5-yl)-ethanone (0.545 mmol) in dry THF (5 mL) was treated dropwise with a 1.0M potassium t-butoxide in THF solution (0.654 mmol). The suspension was stirred at room temperature under nitrogen for 15 minutes. Diethyl oxalate (0.600 mmol) was added, and the brown suspension was diluted with additional THF (6 mL) and allowed to stir at room temperature for 30 minutes. The reaction mixture was quenched by adding glacial acetic acid (0.710 mmol) and ethanol (5 mL). The solvent was removed in vacuo leaving a residual oil that was dissolved in absolute EtOH (5 mL). The ethanolic solution was treated with hydrazine monohydrate (0.655 mmol) and the mixture heated at 80° C. for 1 hour. The resulting yellow suspension was concentrated in vacuo leaving a residual oil that was dissolved in ethyl acetate. This organic phase was washed with water, saturated $NaHCO_3$ and brine, then dried over $MgSO_4$ and evaporated in vacuo to give a yellow oily solid. Silica gel chromatography provided the title compound (59%) as a yellow solid. $^1H$ NMR ($CDCl_3$): δ 1.4 (t, 3H), 1.6–1.9 (6H), 3.1 (m, 4H), 4.4 (q, 2H), 6.9 (broad s, 1H), 7.4–7.5 (m, 3H), 7.9 (m, 2H).

Example 6

4-Methoxymethyl-2-phenyl-thiazole-5-carboxylic acid methyl ester

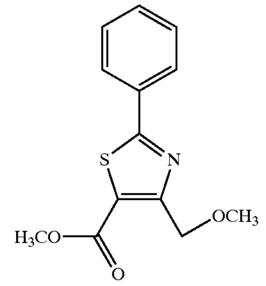

A solution of $CH_3O_2CCH(Cl)COCH_2OCH_3$ (68 mmole, 1.2 eq), prepared according to De Kimpe et al., Synthesis, 188 (1986), in absolute EtOH (75 ml) was treated with thiobenzamide (7.8 g, 56.7 mmole, 1.0 eq) and the resulting brown mixture refluxed under nitrogen for 8 hours. The mixture was partitioned between ethyl acetate and saturated $NaHCO_3$. The organic layer was washed with water twice and brine, then dried over anhydrous sodium sulfate and concentrated in vacuo to give a brown oil. Silica gel chromatography eluting with (9:1) hexanes-ethyl acetate provided 6.98 g (47%) of title compound as a yellow crystalline solid. $^1H$ NMR ($CDCl_3$): δ 3.6 (s, 3H), 3.9 (s, 3H), 4.95 (s, 2H), 7.4–7.5 (m, 3H), 8.0 (m, 2H).

Example 7

4-Methoxymethyl-2-phenyl-thiazole-5-carboxylic acid methoxy-methyl amide

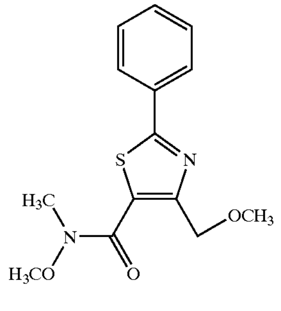

A solution of N,O-dimethylhydroxylamine hydrochloride (13.3 g, 136.3 mmole, 6.0 eq) in dry $CH_2Cl_2$(250 ml) at 0° C. was treated dropwise with neat dimethylaluminum chloride (12.7 ml, 136.3 mmole, 6.0 eq) and the resulting mixture stirred at 0° C. for 2 hours then allowed to warm to RT. To this mixture was added dropwise a solution of the above-prepared 4-methoxymethyl-2-phenyl-thiazole-5-carboxylic acid methyl ester (5.98 g, 22.71 mmole, 1.0 eq) in $CH_2Cl_2$ (20 ml). The yellow mixture was then stirred at room temperature under nitrogen for one hour and re-cooled to 0° C. The mixture was quenched slowly by adding 2.0N NaOH dropwise, warmed to room temperature, and extracted with two portions of $CH_2Cl_2$. The organic phase was washed successively with 1.0N NaOH and brine, dried over $MgSO_4$, and concentrated in vacuo to give a yellow oil. Silica gel chromatography eluting with (4:1) hexanes-ethyl acetate to give 6.5 g (97%) of the title compound as a yellow waxy crystalline solid. $^1H$ NMR ($CDCl_3$): δ 3.35 (s, 3H), 3.5 (s, 3H), 3.7 (s, 3H), 4.95 (s, 2H), 7.4–7.5 (m, 3H), 8.0 (m, 2H).

Example 8

1-(4-Methoxymethyl-2-phenyl-thiazol-5-yl)-ethanone

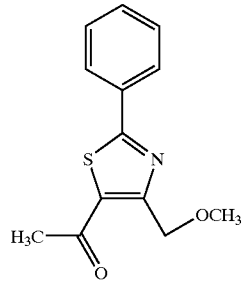

To a solution of the above-prepared 4-methoxymethyl-2-phenyl-thiazole-5-carboxylic acid methoxy-methyl amide (6.706 g, 22.9 mmole, 1.0 eq) in dry THF (25 ml) at 0° C. was added dropwise a solution of 1.4M methylmagnesium bromide in (3:1) toluene-THF (32.7 ml, 45.8 mmole, 2.0 eq). The resulting tan suspension was stirred under nitrogen at room temperature for 30 minutes, then quenched by the addition of saturated ammonium chloride and extracted with ethyl acetate. The organic phase was washed with brine, dried over anhydrous sodium sulfate and concentrated in vacuo to give a brown oil. Silica gel chromatography using a gradient elution of (9:1) to (4:1) hexanes-ethyl acetate provided the title compound (6.033 g, 81%) as a yellow crystalline solid. $^1H$ NMR ($CDCl_3$): δ 2.7 (s, 3H), 3.5 (s, 3H), 4.9 (s, 2H), 7.4–7.5 (m, 3H), 8.0 (m, 2H).

Example 9

5-(4-Methoxymethyl-2-phenyl-thiazol-5-yl)-2H-pyrazole-3-carboxylic acid ethyl ester

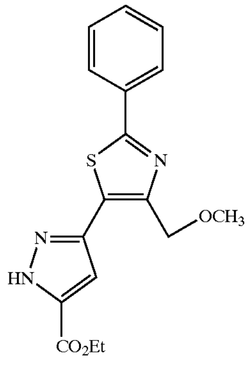

To a solution of the above-prepared 1-(4-methoxymethyl-2-phenyl-thiazol-5-yl)-ethanone (5.22 g, 21.12 mmole, 1.0 eq) in dry THF (100 ml) at −15° C. was added dropwise a solution of 1.0M potassium t-butoxide in THF (31.7 ml, 31.7 mmole, 1.5 eq) and the suspension stirred at room temperature under nitrogen for one hour. Diethyl oxalate (4.4 ml, 31.7 mmole, 1.5 eq) was added, the brown suspension diluted with additional THF (60 ml) and allowed to stir at room temperature for 30 minutes. The mixture was quenched by adding glacial acetic acid (3.2 ml, 2.6 eq). THF was removed in vacuo, and the residual oil was dissolved in absolute ethanol (175 ml) and treated with hydrazine monohydrate (1.4 ml, 30 mmole, 1.4 eq). This mixture was heated at 70° C. for 3 hours. The resulting yellow suspension was concentrated in vacuo leaving a residual oil that was dissolved in ethyl acetate. The organic phase was washed with water, saturated $NaHCO_3$ and brine, then dried over anhydrous sodium sulfate and concentrated in vacuo to give a yellow oily solid. Silica gel chromatography using a gradient elution of (9:1)-(4:1) hexanes-ethyl acetate provided a yellow solid which was triturated with hexanes, filtered and dried in vacuo to give 3.69 g (51%) of the title compound as an off-white solid. $^1H$ NMR ($CDCl_3$): δ 1.4 (t, 3H), 3.5 (s, 3H), 4.4 (q, 2H), 4.8 (s, 2H), 7.0 (s, 1H), 7.4 (m, 3H), 7.9–8.0 (m, 2H).

Example 10

5-(4-Bromomethyl-2-phenyl-thiazol-5-yl)-2H-pyrazole-3-carboxylic acid ethyl ester

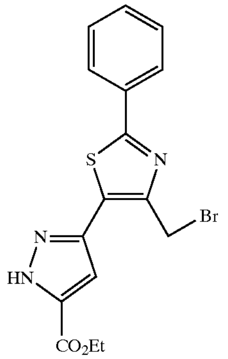

A −78° C. solution of the above-prepared 5-(4-methoxymethyl-2-phenyl-thiazol-5-yl)-2H-pyrazole-3-carboxylic acid ethyl ester (1.5 g, 4.37 mmole, 1.0 eq) in dry $CH_2Cl_2$ (20 ml) was treated with a solution of 1.0M $BBr_3$ in $CH_2Cl_2$ (5.24 ml, 5.24 mmole, 1.2 eq) and the mixture stirred at −78° C. for 45 minutes, then allowed to warm to room temperature and stirred for one hour. The reaction mixture was quenched by adding saturated $NaHCO_3$, stirred for 30 minutes then extracted twice with $CH_2Cl_2$. The organic phase was washed with brine, dried over anhydrous sodium sulfate and concentrated in vacuo to give a yellow solid. Silica gel chromatography using a gradient elution of (3:2)-(1:1) hexanes-ethyl acetate provided 610 mg (36%) of the title compound as an off white solid. $^1H$ NMR ($CDCl_3$): δ 1.4 (t, 3H), 4.4 (q, 2H), 4.9 (s, 2H), 7.2 (s, 1H), 7.4 (m, 3H), 7.95 (m, 2H), 11.1 (bs, 1H).

Example 11

5-(4-Morpholin-4-ylmethyl-2-phenyl-thiazol-5-yl)-2H-pyrazole-3-carboxylic acid ethyl ester

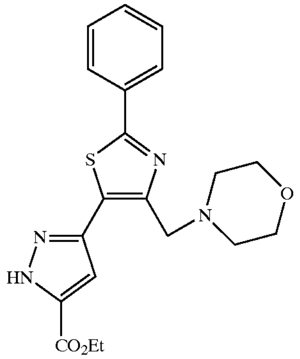

A solution of the above-prepared 5-(4-bromomethyl-2-phenyl-thiazol-5-yl)-2H-pyrazole-3-carboxylic acid ethyl ester (20 mg) in dry THF (1.0 ml) was treated with morpholine (2 drops) and $Et_3N$ (1 drop) and the mixture stirred at room temperature under nitrogen for 2.5 hours. The reaction mixture was partitioned between ethyl acetate and water. The organic layer was washed with brine, dried over anhydrous sodium sulfate and concentrated in vacuo to give an oily solid. Silica gel chromatography using a gradient elution of (9:1)-(4:1) hexanes-acetone provided 18 mg (89%) of the title compound as a white solid. $^1H$ NMR ($CDCl_3$): δ 1.45 (t, 3H), 2.7 (bm, 4H), 3.8 (bm, 4H), 3.9 (s, 2H), 4.45 (q, 2H), 6.95 (s, 1H), 7.45 (m, 3H), 7.9 (m, 2H).

Example 12

1-(2-Phenyl-thiazol-5-yl)-ethanone

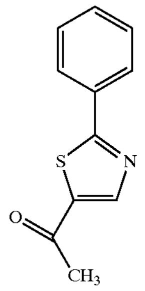

A mixture of 10.0 g (72.9 mmol) of thiobenzamide and 17.4 g (146 mmol) dimethylformamide dimethyl acetal was stirred at room temperature for 2 hours. The volatiles were evaporated under reduced pressure. The residue was dissolved in ethanol (40 ml). To this solution was added 1.0 g (109 mmol) of chloroacetone and the mixture was stirred at room temperature for 3.5 hours. The reaction mixture was diluted with ethyl acetate and washed twice with aqueous sodium bicarbonate, once with water, once with brine and dried over sodium sulfate. The solvent was evaporated under reduced pressure and the residue was purified by chromatography on silica gel using 3:97 acetone:hexanes as eluant to give 3.5 g of the title compound (25%). $^1H$ NMR (500 MHz, $CDCl_3$) δ 8.36 (s, 1H), 8.01 (d, 2H), 7.49 (m, 3H), 2.61 (s, 1H).

Example 13

5-(2-Phenyl-thiazol-5-yl)-2H-pyrazole-3-carboxylic acid ethyl ester

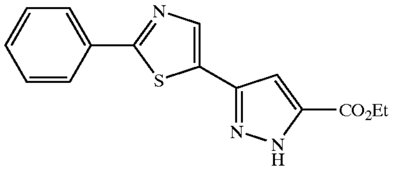

To a solution of 0.10 g (0.49 mmol) of the above-prepared 1-(2-phenyl-thiazol-5-yl)-ethanone was added 0.11 g (0.98 mmol) of 1M potassium tert-butoxide in tetrahydrofuran. The solution was allowed to stir for 0.5 hours. 0.15 g (0.98 mmol) of diethyl oxalate was added and the solution was allowed to stir for 2 hours. The reaction was quenched with aqueous ammonium chloride and partitioned with ethyl acetate. The organic phase was twice washed with aqueous ammonium chloride, once with water, once with brine, and dried over sodium sulfate. The solvent was evaporated under reduced pressure and the residue was dissolved in ethanol (10 ml). To the ethanolic solution was added 0.04 g (0.64 mmol) of glacial acetic acid followed by 0.03 g (0.64 mmol) of hydrazine monohydrate. The solution was allowed to stir for 3 hours at room temperature. The solvent was evaporated under reduced pressure and the residue was purified by chromatography on silica gel using 9:1 hexanes:ethyl acetate as eluant to give 75 mg of the title compound (51%). $^1$H NMR (500 MHz, $CDCl_3$) δ 8.10 (s, 1H) 7.98 (m, 2H) 7.47 (m, 3H) 7.10 (s, 1H) 4.42 (q, 2H) 1.42 (t, 3H).

Example 14

4-Bromo-5-(2-phenyl-thiazol-5-yl)-2H-pyrazole-3-carboxylic acid ethyl ester

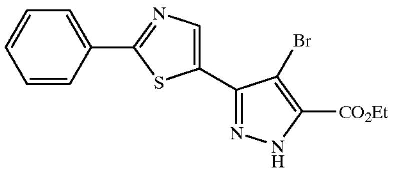

To a mixture of 0.03 g (0.10 mmol) of the above-prepared 5-(2-phenyl-thiazol-5-yl)-2H-pyrazole-3-carboxylic acid ethyl ester in acetonitrile (2 ml) and dimethylformamide (1.5 ml) was added 0.02 g (0.10 mmol) of N-bromosuccinamide. The reaction was allowed to stir for 2 hours and diluted with ethyl acetate. The solution was washed 3 times with aqueous sodium bicarbonate, once with brine, and dried over sodium sulfate. The solvent was evaporated under reduced pressure and the residue was purified by chromatography on silica gel using 9:1 hexanes:ethyl acetate as eluant to give 28 mg of the title compound (746). $^1$H NMR (500 MHz, $CDCl_3$) δ 8.53 (s, 1H) 8.01 (d, 2H) 7.48 (m, 3H) 4.47 (q, 2H) 1.44 (t, 3H).

Example 15

4-Chloro-5-(2-phenyl-thiazol-5-yl)-2H-pyrazole-3-carboxylic acid ethyl ester

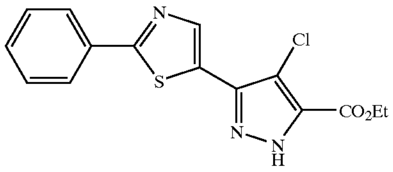

To a solution of 25 mg (0.084 mmol) of the above-prepared 5-(2-phenyl-thiazol-5-yl)-2H-pyrazole-3-carboxylic acid ethyl ester in dichloromethane was added 23 mg (0.168 mmol) of sulfuryl chloride and allowed to stir overnight at room temperature. The solution was diluted with ethyl acetate, washed once with aqueous sodium bicarbonate, once with water once with brine and dried over sodium sulfate. The solvent was evaporated under reduced pressure and the residue was purified by chromatography on silica gel using 7:93 ethyl acetate:hexanes as eluant to give 23 mg of the title compound (82%). $^1$H NMR (500 MHz, $CDCl_3$) δ 8.39 (s, 1H) 7.94 (d, 2H) 7.40 (m, 2H) 4.40 (q, 2H) 1.38 (t, 3H).

Example 16

4-Chloro-5-(2-phenyl-thiazol-5-yl)-2H-pyrazole-3-carboxylic acid ethyl amide

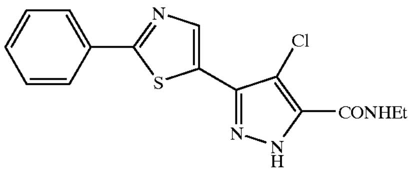

To 15 mg (0.045 mmol) of the above-prepared 4-chloro-5-(2-phenyl-thiazol-5-yl)-2H-pyrazole-3-carboxylic acid ethyl ester was added 45 mg (1.0 mmol) of 2M ethylamine in tetrahydrofuran followed by the addition of 2 drops of water. The mixture was heated to 60° C. in a sealed tube and allowed to stir overnight. The solvent was evaporated under reduced pressure and the residue was purified by chromatography on silica gel using 2:5 ethyl acetate:hexanes as eluant to give 5 mg of the title compound (33%). $^1$H NMR (500 MHz, $CDCl_3$) δ 8.39 (s, 1H) 8.00 (d, 2H) 7.47 (m, 3H) 6.78 (m, 1H) 3.58 (m, 2H) 1.32 (t, 3H).

Example 17

2-Phenyl-thiazole-5-carboxylic Acid Methoxy-methyl-amide

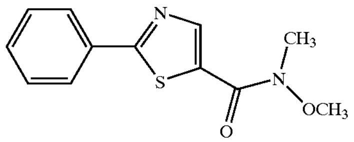

To a solution of 3.72 g (93 mmol) of sodium hydroxide in water (20 ml) at 0° C. was added 3.72 g (23.2 mmol) of bromine dropwise. The reaction was allowed to warm to room temperature and stir for 15 minutes. The solution was added to 1.05 g (5.17 mmol) of the above-prepared 1-(2-phenyl-thiazol-5-yl)-ethanone in dioxane (50 ml) and allowed to stir for 3 hours. The solution was poured onto ice, acidified with 1N hydrochloric acid, and was twice extracted with ethyl acetate. The combined organics were dried over magnesium sulfate and the solvent was evaporated under reduced pressure to give 1.01 g (4.9 mmol) of the carboxylic acid. To the acid in THF (10 ml) was added 1.04 g (6.4 mmol) of 1,1-carbonyldiimidazole. The solution was heated to 50° C. and allowed to stir for 1 hour. The solution was cooled to room temperature. 0.79 g (7.9 mmol) of triethylamine and 0.672 g (6.9 mmol) of N,O-dimethylhydroxylamine hydrochloride was added and allowed to stir overnight. The solution was diluted with ethyl acetate and washed once with aqueous potassium hydrogen sulfate, once with water, once with brine and dried over sodium sulfate. The solvent was evaporated under reduced pressure and the residue was purified by chromatography on silica gel using 7:93 ethyl acetate:hexanes as eluant to give 0.66 g of the title compound (54%). $^1$H NMR (500 MHz, $CDCl_3$) δ 8.58 (s, 1H) 8.00 (m, 2H) 7.46 (m, 3H) 3.82 (s, 3H) 3.40 (s, 3H).

Example 18

1-(2-Phenyl-thiazol-5-yl)-propan-1-one

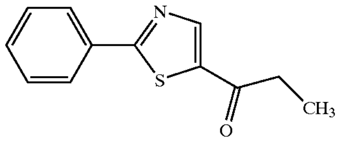

To a solution of 0.32 g (1.3 mmol) of the above-prepared 2-phenyl-thiazole-5-carboxylic acid methoxy-methyl-amide in tetrahydrofuran at room temperature was added 0.34 g (2.6 mmol) of IM ethyl magnesium bromide in tetrahydrofuran. The reaction mixture was allowed to stir for one hour. The reaction was quenched with aqueous ammonium chloride and partitioned with ethyl acetate. The organic phase was washed once with aqueous ammonium chloride, once with water, once with brine and dried over sodium sulfate. The solvent was evaporated under reduced pressure and the residue was purified by chromatography on silica gel using 1:19 ethyl acetate:hexanes to give 0.26 g of the title compound (93%). $^1$H NMR (500 MHz, $CDCl_3$) δ 8.36 (s, 1H) 8.0 (m, 2H) 7.49 (m, 3H) 2.98 (q, 2H) 1.27 (t, 3H).

Example 19

2-Hydroxy-3-methyl-4-oxo-4-(2-phenyl-thiazol-5-yl)-butyric acid ethyl ester

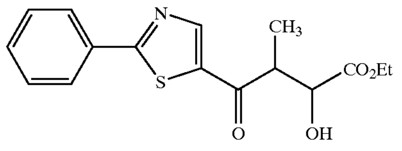

To a −78° C. solution of 0.26 g (1.2 mmol) of the above-prepared 1-(2-phenyl-thiazol-5-yl)-propan-1-one was added 0.24 g (1.4 mmol) of 1M lithium bis(trimethylsilyl) amide in tetrahydrofuran. The mixture was allowed to stir for 0.5 hours and then 0.38 g (1.5 mmol) of 1M chlorotitanium triisopropoxide in hexanes was added. The reaction was allowed to warm to −20° C. and stirred for 15 minutes. The reaction was recooled to −78° C. and 0.25 g (0.24 mmol) of ethyl glyoxalate in toluene (50%) was added. The solution was warmed to room temperature and allowed to stir for 0.5 hours. The reaction was quenched with aqueous potassium sodium tartrate tetrahydrate and partitioned with ethyl acetate. The organic phase was twice washed with aqueous potassium sodium tartrate tetrahydrate, once with water, once with brine and dried over sodium sulfate. The solvent was evaporated under reduced pressure and the residue was purified by chromatography on silica gel using 1:9 ethyl acetate:hexanes to give 0.15 g of the title compound (40%). $^1$H NMR (500 MHz, $CDCl_3$) δ 8.42 (s, 1H) 8.01 (d, 2H) 7.48 (m, 3H) 5.8 (m, 1H) 4.27 (q, 2H) 3.75 (m, 1H) 3.28 (m, 1H) 1.37 (d, 3H) 1.26 (t, 3H).

Example 20

4-Methyl-5-(2-phenyl-thiazol-5-yl)-2H-pyrazole-3-carboxylic acid ethyl ester

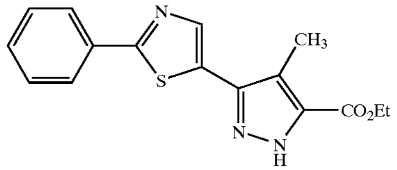

A mixture of 0.39 g (0.91 mmol) of Dess-Martin periodinane and 0.07 g (0.91 mmol) of tert-butyl alcohol in dichloromethane (2 ml) was allowed to stir at room temperature for 20 minutes. The solution was cooled to 0° C. and to this was added 0.15 g (0.45 mmol) of the above-prepared 2-hydroxy-3-methyl-4-oxo-4-(2-phenyl-thiazol-5-yl)-butyric acid ethyl ester in dichloromethane (2 ml). The reaction was stirred at 0° C. for 3 hours and quenched with sodium bisulfite in 50% aqueous sodium bicarbonate. The mixture was diluted with dichloromethane and allowed to stir for 20 minutes at room temperature. The organic phase was washed twice with aqueous sodium bicarbonate, once with water, once with brine, and dried over sodium sulfate. The solvent was evaporated under reduced pressure and dissolved in ethyl alcohol (5 ml). 41 mg (0.68 mmol) of glacial acetic acid was added followed by the addition of 34 mg (0.68 mmol) of hydrazine monohydrate. The solution was allowed to stir at room temperature for 4 hours. The solvent was evaporated under reduced pressure and the residue was purified by chromatography on silica gel using 1:99 ethyl alcohol:dichloromethane as eluant to give 0.035 g of the title compound (25%). $^1$H NMR (500 MHz, $CDCl_3$) δ 8.08 (s, 1H) 8.00 (d, 2H) 7.47 (m, 3H) 4.45 (q, 2H) 2.54 (s, 3H) 1.44 (t, 3H).

Example 21

4-Methyl-2-phenyl-oxazole-5-carboxylic acid methoxy-methyl-amide

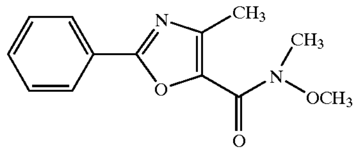

A suspension of commercially available N-benzoyl-DL-alanine (3.0 g, 15.5 mmole, 1.0 eq) in dry benzene (62 ml) and dry dichloromethane (23 ml) was treated dropwise with neat oxalyl chloride (13.5 ml, 155 mmole, 10 eq) and the white suspension stirred overnight under nitrogen at room temperature. The resulting homogeneous yellow mixture was then evaporated in vacuo to an oil, azeotroped twice with benzene and evaporated to give crude acid chloride as a yellow oil. This was used immediately in next step without further purification. See Crooks et al., J. Chem. Soc., Chem. Comm., 2335 (1995).

A 0° C. solution of the above crude acid chloride (15.5 mmole, 1.0 eq) in dry THF (50 ml) was treated with N,O-dimethylhydroxylamine hydrochloride (2.27 g, 23.3 mmole, 1.5 eq) followed by $Et_3N$ (6.5 ml, 46.5 mmole, 3.0 eq) and the dark brown suspension was stirred overnight under nitrogen. The mixture was partitioned between ethyl acetate and water. The organic phase was washed successively with 5% $KHSO_4$ solution, water and brine, then dried over anhydrous sodium sulfate. Concentration in vacuo provided a crude brown oil. The crude oil was chromatographed on silica gel using a gradient elution of (4:1) to (7:3) hexanes-ether to give 1.82 g (48%) of the title compound as a yellow crystalline solid. $^1H$ NMR: ($CDCl_3$) δ 2.5 (s, 3H), 3.35 (s, 3H), 3.9 (s, 3H), 7.4–7.5 (m, 3H), 8.05 (m, 2H).

Example 22

[4-(4-Methyl-2-phenyl-oxazol-5-yl)-4-oxo-but-2-ynyl]-carbamic acid tert-butyl ester

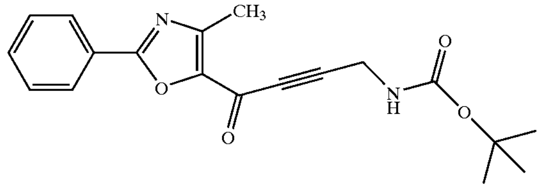

A −15° C. solution of N-BOC propargyl amine (651 mg, 4.2 mmole, 3.5 eq) in dry THF (12 ml) was treated dropwise with a 1.6M n-BuLi in hexanes solution (5.25 ml, 8.4 mmole, 7.0 eq) and the pale yellow dianion solution was stirred at −15° C. for 30 minutes under nitrogen. A dry THF solution (3 ml) of the above-prepared 4-methyl-2-phenyl-oxazole-5-carboxylic acid methoxy-methyl-amide (296 mg, 1.2 mmole, 1.0 eq) was added dropwise to the dianion solution at −15° C. and the mixture stirred at 0° C. for 2 hours under nitrogen. The mixture was quenched by adding a solution of 2M $NaH_2PO_4$ (5 ml), warmed to room temperature, and then extracted with ethyl acetate. The organic phase was washed with water and brine then dried over anhydrous sodium sulfate and concentrated in vacuo to provide the title compound as a crude brown oil. The crude oil was used immediately in the next step without further purification.

Example 23

[5-(4-Methyl-2-phenyl-oxazol-5-yl)-2H-pyrazol-3-ylmethyl]-carbamic acid tert-butyl ester

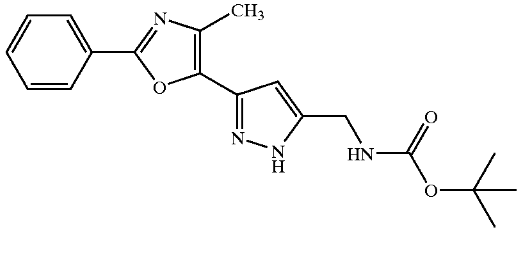

A solution of the above-prepared [4-(4-methyl-2-phenyl-oxazol-5-yl)-4-oxo-but-2-ynyl]-carbamic acid tert-butyl ester (~1.2 mmole) in absolute ethanol (7 ml) was treated with excess hydrazine monohydrate (6 drops) and the brown mixture stirred at room temperature for 30 minutes. The mixture was evaporated in vacuo to an oil and chromatographed on silica gel using a gradient elution of (4:1) hexanes-ethyl acetate. Obtained 258 mg (61%) of 3 as a pale yellow solid with good $^1H$ NMR ($CDCl_3$): ∂ 1.55 (s, 9H), 2.5 (s, 3H), 4.35 (d, 2H), 5.2 (bt, 1H), 6.45 (s, 1H), 7.4–7.5 (m, 3H), 8.05 (m, 2H).

Example 24

C-[5-(4-Methyl-2-phenyl-oxazol-5-yl)-2H-pyrazol-3-yl]-methylamine

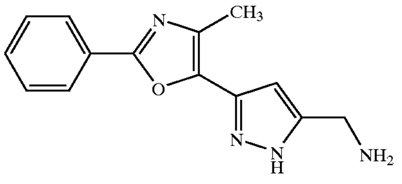

A solution of the above-prepared [5-(4-Methyl-2-phenyl-oxazol-5-yl)-2H-pyrazol-3-ylmethyl]-carbamic acid tert-butyl ester (258 mg, 0.728 mmole, 1.0 eq) in dry $CH_2Cl_2$ (4 ml) was treated with trifluoroacetic acid (1 ml, excess) and the brown homogeneous mixture stirred under nitrogen at room temperature for one hour. The mixture was partitioned between $CH_2Cl_2$ and 1.0N NaOH, the organic phase washed with brine, dried over anhydrous sodium sulfate and concentrated in vacuo to give 177 mg (96%) of the title compound as an off-white solid. The crude solid was used without further purification.

Example 25

[5-(4-Methyl-2-phenyl-oxazol-5-yl)-2H-pyrazol-3-ylmethyl]-carbamic acid ethyl ester

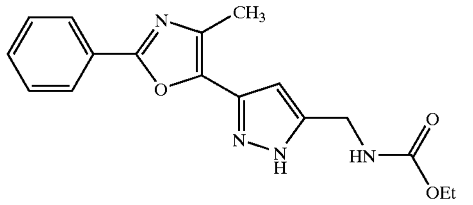

A heterogeneous mixture of the above-prepared C-[5-(4-Methyl-2-phenyl-oxazol-5-yl)-2H-pyrazol-3-yl]-methylamine (31 mg, 0.122 mmole, 1.0 eq) in ethyl acetate (0.5 ml) and 1.0N $NaHCO_3$ (0.5 ml) was treated with excess methyl chloroformate (5 drops) and the mixture stirred at room temperature for 30 minutes. The mixture was partitioned between ethyl acetate and saturated $NaHCO_3$. The organic phase was washed with water and brine, then dried over anhydrous sodium sulfate and evaporated in vacuo to give a yellow solid. Silica gel chromatography eluting with (4:1) hexanes-acetone provided 28 mg (74%) of the title compound as a white solid. $^1H$ NMR (DMSO-$d_6$): δ 2.6 (s, 3H), 3.6 (s, 3H), 4.25 (m, 2H), 6.5 (s, 1H), 7.5 (m, 3H), 7.7 (bm, 1H), 8.0 (m, 2H).

Example 26

2,4-Diphenyl-oxazole-5-carboxylic acid ethyl ester

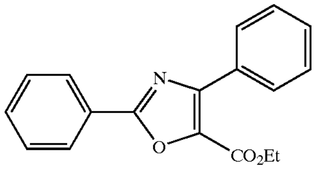

The starting ketoester $PhCOCH(Cl)CO_2Et$ was prepared according to De Kimpe, et al., *Synthesis*, 188 (1986). The starting ketoester (~27 mmole, 1.08 eq) and benzamide (3.0 g, 25.0 mmole, 1 eq) were heated neat at 150° C. for 4 hours. The mixture was then partitioned between $CH_2Cl_2$ and saturated $NaHCO_3$. The organic phase was washed with water and brine, dried over anhydrous sodium sulfate and concentrated in vacuo. Residual benzamide was precipitated out with ether. The filtrate was concentrated and then chromatographed on silica gel eluting with (95:5) hexanes-ether to provide 500 mg of the title compound as a white solid. $^1H$-NMR ($CDCl_3$): δ 1.4 (t, 3H), 4.4 (q, 2H), 7.4–7.6 (m, 3H), 8.1 (dd, 1H), 8.25 (dd, 1H).

Example 27

2,4-Diphenyl-oxazole-5-carboxylic acid

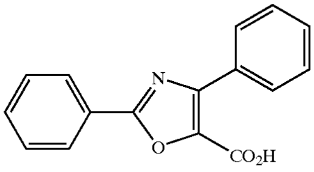

A solution of the above-prepared 2,4-diphenyl-oxazole-5-carboxylic acid ethyl ester (500 mg, 1.70 mmole, 1.0 eq) in dioxane (6 ml) was treated with 2N NaOH (1.7 ml, 3.4 mmole, 2.0 eq) and the mixture stirred at room temperature overnight under nitrogen. The mixture was then partitioned between ethyl acetate and 2.0N HCl. The organic phase washed with 0.5N HCl and brine, dried over anhydrous sodium sulfate and concentrated in vacuo to give 426 mg of the title compound as a crude yellow solid. The product was used directly in the next step, without purification.

Example 28

2,4-Diphenyl-oxazole-5-carboxylic acid methoxy-methyl-amide

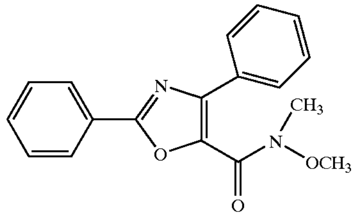

A solution of the above-prepared 2,4-diphenyl-oxazole-5-carboxylic acid (427 mg, 1.61 mmole, 1.0 eq) in dry THF was treated with carbonyldiimidazole (340 mg, 2.09 mmole, 1.3 eq) and the mixture heated at 50° C. for 3 hours. Triethylamine (360 uL, 2.58 mmole, 1.6 eq) and N,O-dimethylhydroxylamine-HCl (236 mg, 2.42 mmole, 1.5 eq) were added and the mixture heated at 50° C. for 3 hours. The mixture was partitioned between ethyl acetate and water. The organic phase was washed with 5% $KHSO_4$ and brine, dried over anhydrous sodium sulfate and concentrated in vacuo to a brown oil. The crude oil was chromatographed on silica gel eluting with (7:3) hexanes-ether to give 371 mg (75%) of the title compound as a brown crystalline solid. $^1H$ NMR ($CDCl_3$) δ 3.35 (s, 3H), 3.8 (s, 3H), 7.3–7.6 (m, 6H), 7.95 (dd, 2H), 8.15 (dd, 2H).

Example 29

[4-(2,4-Diphenyl-oxazol-5-yl)-4-oxo-but-2-ynyl]-carbamic acid tert-butyl ester

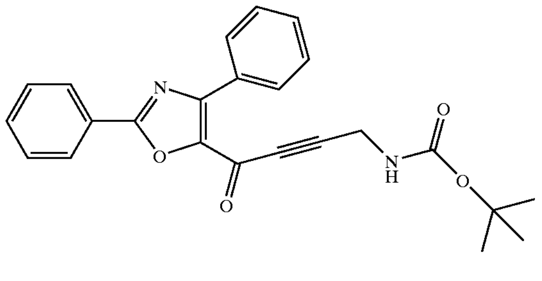

A −15° C. solution of N-BOC propargyl amine (641 mg, 4.13 mmole, 3.5 eq) in dry THF (12 ml) was treated dropwise with a 1.6M n-BuLi in hexanes solution (5.16 ml, 8.3 mmole, 7.0 eq) and the resulting pale yellow dianion solution stirred at −15° C. for 30 minutes under nitrogen. A dry THF solution (3 ml) of the above-prepared 2,4-Diphenyl-oxazole-5-carboxylic acid methoxy-methyl-amide (365 mg, 1.18 mmole, 1.0 eq) was added dropwise to the dianion solution at −15° C. and the mixture stirred at 0° C. for 2 hours under nitrogen. The mixture was quenched by adding a solution of 2M $NaH_2PO_4$ (5 ml), then warmed to room temperature and extracted with ethyl acetate. The organic phase was washed with water and brine then dried over anhydrous sodium sulfate and concentrated in vacuo to give the title compound as a crude brown oil. The crude oil without purification was used immediately in next step.

Example 30

[5-(2,4-Diphenyl-oxazol-5-yl)-2H-pyrazol-3-ylmethyl]-carbamic acid tert-butyl ester

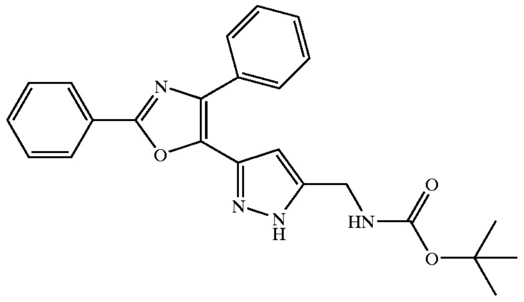

A solution of the above-prepared [4-(2,4-diphenyl-oxazol-5-yl)-4-oxo-but-2-ynyl]-carbamic acid tert-butyl ester (~1.2 mmole) in absolute ethanol (7 ml) was treated with excess hydrazine monohydrate (6 drops) and the brown mixture stirred at room temperature overnight. The mixture was concentrated in vacuo to an oil and chromatographed on silica gel eluting with (4:1) hexanes-ethyl acetate. The title compound (251 mg) was obtained as a pale yellow solid. $^1H$ NMR ($CDCl_3$): δ 1.50 (s, 9H), 2.5 (s, 3H), 4.3 (m, 2H), 5.2 (bt, 1H), 6.5 (s, 1H), 7.3–7.5 (m, 6H), 7.9 (m, 2H), 8.15 (m, 2H).

Example 31

[5-(2,4-Diphenyl-oxazol-5-yl)-2H-pyrazol-3-ylmethyl]-carbamic acid methyl ester

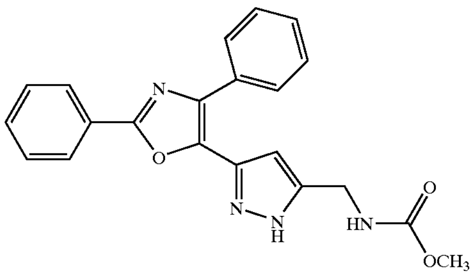

A solution of the above-prepared [5-(2,4-Diphenyl-oxazol-5-yl)-2H-pyrazol-3-ylmethyl]-carbamic acid tert-butyl ester (251 mg, 1.0 eq) in dry $CH_2Cl_2$ (8 ml) was treated with trifluoroacetic acid (2 ml, excess) and the brown homogeneous mixture stirred under nitrogen at room temperature for 1.5 hours. The mixture was partitioned between $CH_2Cl_2$ and 1.0N NaOH. The organic phase was washed with brine, dried over anhydrous sodium sulfate and concentrated in vacuo to give 181 mg of crude benzylamine as a light brown solid. The crude benzylamine was used without further purification. A heterogeneous mixture of benzylamine (32 mg, 0.101 mmole, 1.0 eq) in ethyl acetate (1.5 ml) and 1.0N $NaHCO_3$ (1.5 ml) was treated with excess methyl chloroformate (5 drops) and the mixture stirred at room temperature for 30 minutes. The mixture was partitioned between ethyl acetate and saturated $NaHCO_3$. The organic phase was washed with water and brine, then dried over anhydrous sodium sulfate and concentrated in vacuo to give a yellow oil. Chromatography on silica gel with a gradient elution of (85:15) to (4:1) hexanes-acetone provided 24 mg of the title compound as a white solid. $^1H$ NMR (DMSO-$d_6$): δ 3.6 (s, 3H), 4.3 (3, 2H), 6.5 (s, 1H), 7.35–7.6 (m, 6H), 7.7 (bm, 1H), 8.1 (m, 2H), 8.2 (m, 2H).

Example 32

5-Phenyl-2H-pyrazole-3-carboxylic acid ethyl ester

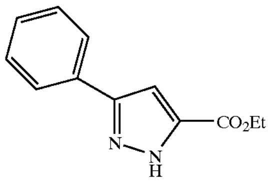

To a room temperature mixture of acetophenone (1.0 mL, 8.57 mmoles) and diethyl oxalate (1.75 mL, 12.86 mmoles) in THF (15 mL) was added potassium t-butoxide (8.57 mL of a 1.0 M solution in t-BuOH) under a nitrogen atmosphere. The resulting dark mixture was stirred at room temperature for two hours. The crude reaction was then diluted with ethyl acetate, quenched with 6 N HCl, and then diluted with brine and enough water to dissolve all solids. The phases were separated and the organic phase was dried over $Na_2SO_4$, filtered, and concentrated in vacuo. The crude diketoester was diluted EtOH (10 mL), then treated sequentially with acetic acid (2 mL) and hydrazine (1 mL) and stirred at room temperature for 1 hour. The crude reaction was concentrated in vacuo to a thick oil, diluted with ethyl acetate, washed sequentially with water and brine, dried over $Na_2SO_4$, filtered, concentrated in vacuo, and flash chromatographed (silica gel, hexanes/ethyl acetate gradient) to give the title compound (1.76 g, 95% yield) as a yellow solid. $^1H$ NMR ($CDCl_3$, 400 MHz): 7.83 (d, 2H); 7.25 (dd, 2H); 7.28 (dd, 1H); 7.09 (s, 1H); 4.59 (q, 2H); 1.39 (t, 3H).

Example 33

2-Ethyl-5-phenyl-2H-pyrazole-3-carboxylic acid ethyl ester

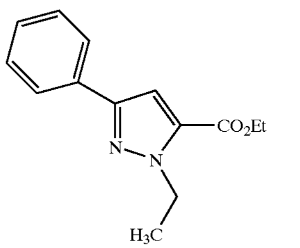

To a 0° C. mixture of the above-prepared 5-phenyl-2H-pyrazole-3-carboxylic acid ethyl ester (350 mg, 1.62 mmoles) and iodoethane (260 μL, 3.23 mmoles) in DMF (3 mL) was added neat LiH (spatula tip, excess) under a nitrogen atmosphere. The resulting mixture was warmed up to room temperature and stirred overnight. The crude reaction was cooled to 0° C., quenched with aqueous $NH_4Cl$, diluted with ethyl acetate and enough water to dissolve all solids. The phases were separated, and the organic phase was washed sequentially with water and brine, dried over $Na_2SO_4$, filtered, and concentrated in vacuo. The regioisomeric products separated and purified by flash chromatography (silica gel, hexanes/ethyl acetate gradient) to give the title compound (167 mg, 42% yield, higher Rf in hexanes/ethyl acetate) and the undesired regioisomer (175 mg, 44% yield) as white solids. $^1H$ NMR ($CDCl_3$, 400 MHz): 7.81 (d, 2H); 7.40 (dd, 2H); 7.29 (dd, 1H); 7.13 (s, 1H); 4.63 (q, 2H); 4.37 (q, 2H); 1.47 (t, 3H); 1.41 (t, 3H).

Example 34

2-Ethyl-5-phenyl-2H-pyrazole-3-carboxylic acid methoxy-methyl-amide

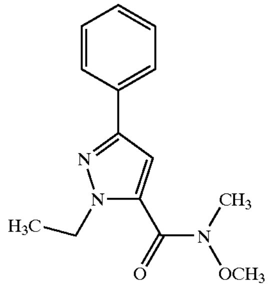

To a room temperature solution of the above-prepared 2-ethyl-5-phenyl-2H-pyrazole-3-carboxylic acid ethyl ester (165 mg, 675 μmoles) in MeOH (2 mL) was added aqueous NaOH (215 μL of a 10 N solution, 215 μmoles) under a nitrogen atmosphere. The resulting mixture was allowed to stir at room temperature overnight. The reaction was acidified with 6 N HCl, diluted with ethyl acetate and brine, and the phases were separated. The organic phase was dried over $Na_2SO_4$, filtered, and concentrated in vacuo. The crude acid was suspended in THF (2 mL), and carbonyldiimidazole was added (140 mg, 860 μmoles), and the mixture was stirred overnight at room temperature. The resulting acylimidazolide was treated with a preformed mixture of MeON(H)Me.HCl (140 mg, 1.43 mmole) and isopropylethylamine (250 μL, 1.43 mmoles) in DMF (1 mL) and the resulting mixture heated to 90° C. overnight. The reaction was then cooled to room temperature and diluted with ethyl acetate. The organic layer was washed with 1 M $NaHSO_4$ (3×), brine, dried over $Na_2SO_4$, filtered, and concentrated in vacuo. Flash chromatography (silica gel, hexanes/ethyl acetate gradient) provided the title compound (130 mg, 74% yield) as a thick oil.

Example 35

[4-(2-Ethyl-5-phenyl-2H-pyrazol-3-yl)-4-oxo-but-2-ynyl]-carbamic acid tert-butyl ester

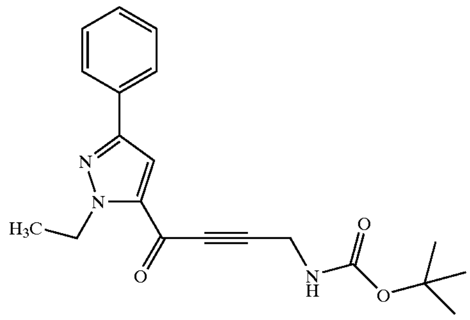

To a −10° C. solution of N-t-butoxycarbonyl propargylamine (502 mg, 3.24 mmoles) in THF (5 mL) was added nBuLi (3.7 mL of a 1.6 M solution in hexanes, 5.94 mmoles) dropwise over 10 minutes. The resulting dianion mixture was stirred at −10° C. for 15 minutes, then treated with a THF solution (2 mL) of the above-prepared 2-ethyl-5-phenyl-2H-pyrazole-3-carboxylic acid methoxy-methyl-amide (125 mg, 482 μmoles), allowed to warm to room temperature, and stirred at room temperature for 2 hours. The resulting mixture was cooled to 0° C., quenched with 2 M $NaH_2PO_4$, diluted with ethyl acetate, and vigorously stirred for 5 minutes. The phases were separated, the organic phase dried over $Na_2SO_4$, filtered, and concentrated in vacuo. The crude title compound was used directly in the next step.

Example 36

(2'-Ethyl-5'-phenyl-1H,2'H-[3,3']bipyrazolyl-5-ylmethyl)-carbamic acid tert-butyl ester

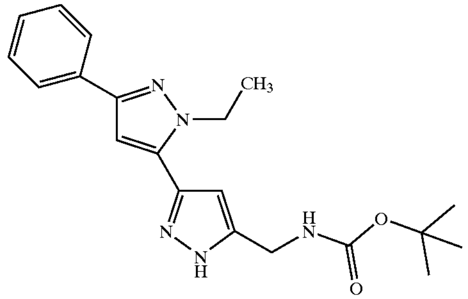

To the above-prepared [4-(2-ethyl-5-phenyl-2H-pyrazol-3-yl)-4-oxo-but-2-ynyl]-carbamic acid tert-butyl ester in EtOH (5 mL), hydrazine monohydrate was added (excess, 5 drops), and the mixture was stirred at room temperature for 2 hours. The resulting mixture was concentrated in vacuo to a thick oil, diluted with ethyl acetate, washed sequentially with water and brine, dried over $Na_2SO_4$, filtered, and concentrated in vacuo. Flash chromatography (silica gel, hexanes/ethyl acetate gradient) provided the title compound (175 mg, 98% yeild) as a white foam. $^1$H NMR ($CDCl_3$, 400 MHz): 7.86 (d, 2H); 7.39 (dd, 2H); 7.28 (dd, 1H); 6.72 (s, 1H); 6.36 (s, 1H); 5.12 (broad dd, 1H); 4.58 (q, 2H); 4.31 (d, 2H); 1.49 (s, 9H).

Example 37

(2'-Ethyl-5'-phenyl-1H,2'H-[3,3']bipyrazolyl-5-ylmethyl)-carbamic acid methyl ester

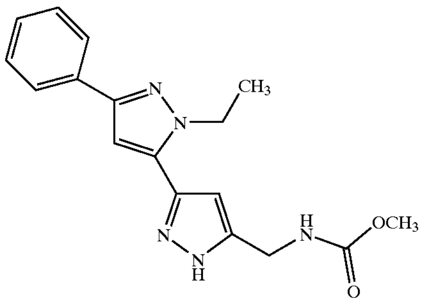

To a room temperature solution of the above-prepared (2'-ethyl-5'-phenyl-1H,2'H-[3,3']bipyrazolyl-5-ylmethyl)-carbamic acid tert-butyl ester (25 mg, 68 μmoles) in $CH_2Cl_2$ (2 mL) was added trifluoroacetic acid (0.5 mL, excess). The resulting solution was stirred at room temperature for one hour, then concentrated and azeotroped with acetonitrile (3×) in vacuo. To the resulting crude deprotection product in acetonitrile was added triethylamine, then 1-methoxycarbonyl imidazole (26 mg, 204 μmoles) and the mixture was heated to 90° C. for two hours. The reaction was then cooled to room temperature, diluted with ethyl acetate and 1 M $NaHSO_4$, and stirred vigorously for 20 minutes. The organic phase was washed with brine, dried over $Na_2SO_4$, filtered, and concentrated in vacuo. Flash chromatography (silica gel, hexanes/ethyl acetate gradient) provided the title compound as a white solid. $^1$H NMR ($CDCl_3$, 400 MHz): 7.87 (d, 2H); 7.41 (dd, 2H); 7.37 (dd, 1H); 6.75 (s, 1H); 6.42 (s, 1H); 5.30 (dd, 1H); 4.68 (q, 2H); 4.40 (d, 2H); 3.73 (s, 3H); 1.51 (t, 3H).

Example 38

1'-(3-Chloro-phenyl)-5'-methyl-1H,1'H-[3,4']bipyrazolyl-5-carboxylic acid ethyl ester (Compound ID-28)

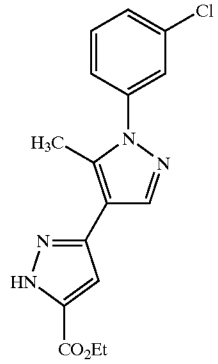

To a solution of 47 mg (0.2 mmol) of 1-[1-(3-chlorophenyl)-5-methyl-1H-pyrazol-4-yl]ethan-1-one (commercially available) in 2 mL of THF was added successively 0.4 mL (0.4 mmol) of 1M KOtBu in THF and 54 μL (0.4 mmol) of diethyl oxalate. The mixture was stirred at room temperature overnight, quenched with water, and diluted with ethyl acetate. The solution was washed successively with saturated aqueous ammonium chloride, saturated aqueous sodium bicarbonate, and brine, dried over sodium sulfate, and concentrated in vacuo. The residue was diluted with 2 mL of ethanol, and 15 mL (0.3 mmol) of hydrazine monohydrate was added followed by 15 mL (0.3 mmol) of acetic acid. The mixture was stirred at room temperature for 2 hours, and concentrated in vacuo. The residue was purified by reverse phase preparative HPLC to afford 8 mg of the title compound as the trifluoroacetic acid salt. MS m/e expected M+1 333.18, found m/e 333.01. $^1$H NMR (DMSO-$d_6$) δ 14.0 (s, 0.45H), 13.8 (s, 0.55H), 8.05 (s, 1H), 7.75 (s, 1H), 7.55 (m, 3H), 7.1 (br s, 0.45H), 6.8 (br s, 0.55H), 4.3 (br s, 2H), 2.65 (br s, 1.4H), 2.4 (br s, 1.6H), 1.3 (t, 3H).

Biological Methods

Method A. Susceptibility Testing in Liquid Media

Compounds of this invention may also be tested for antimicrobial activity by susceptibility testing in liquid media. Such assays may be performed within the guidelines of the latest NCCLS document governing such practices: "M7-A5 Methods for dilution Antimicrobial Susceptibility Tests for Bacteria that Grow Aerobically; Approved Standard—Fifth Edition (2000)". Other publications such as "Antibiotics in Laboratory Medicine" (Edited by V. Lorian, Publishers Williams and Wilkins, 1996) provide essential practical techniques in laboratory antibiotic testing. Essentially, several discrete bacterial colonies (3 to 7) from a freshly streaked plate are transferred to an appropriate rich broth medium such as MHB, supplemented where appropriate for the more fastidious organisms. This is grown overnight to high density followed by a 1 or 2-thousand-fold dilution to give an inoculation density of between $5\times10^5$ and $5\times10^6$ CFU per mL. Alternatively, the freshly picked colonies can be incubated at 37C for about 4 to 8 hrs until the culture equals or exceeds a turbidity of a 0.5 McFarland standard (approximately $1.5\times10^8$ cells per mL) and diluted to give the same CFU per mL as above. In a more convenient method, the inoculum can be prepared using a commercially available mechanical device (the BBL PROMPT System) that involves touching five colonies directly with a wand, containing crosshatch grooves at its bottom, followed by suspension of the bacteria in an appropriate volume of saline. Dilution to the appropriate inoculum cell density can be made from this cell suspension. The broth used for testing consists of MHB supplemented with 50 mg per L of $Ca^{2+}$ and 25 mg per L of $Mg^{2+}$. Standard dilution panels of control antibiotics are made and stored as in the NCCLS standard M7-A5, the dilution range typically being in the 128 $\mu$g per mL to 0.015 $\mu$g per mL (by 2-fold serial dilution). The test compounds are dissolved and diluted fresh for experimentation on the same day; the same or similar ranges of concentration as above being used. The test compounds and controls are dispensed into a multiwell plate and test bacteria added such that the final inoculation is approximately $5\times10^4$ CFU per well and the final volume is 100 $\mu$L. The plates are incubated at 35C overnight (16 to 20 hr) and checked by eye for turbidity using a test reading mirror or quantitated with a multiwell plate reader. The endpoint minimal inhibitory concentration (MIC) is the lowest concentration of drug at which the microorganism tested does not grow. Such determinations are also compared to the appropriate tables contained in the above two publications to ensure that the range of antibacterial activity is within the acceptable range for this standardized assay.

Selected compounds of this invention were found to be active in the above Susceptibility Testing in Liquid Media.

Method B. ATPase Assay

The ATP hydrolysis activity of DNA gyrase was measured by coupling the production of ADP through pyruvate kinase/lactate dehydrogenase to the oxidation of NADH. This method has been described previously. (Tamura and Gellert, 1990, J. Biol. Chem. 265, 21342–21349).

ATPase assays were carried out at 30° C. in buffered solutions containing 100 mM TRIS pH 7.6, 1.5 mM $MgCl_2$, and 150 mM KCl. The coupling system contained (final concentrations) 2.5 mM phosphoenol pyruvate, 200 $\mu$M nicotinamide adenine dinucleotide (NADH), 1 mM DTT, 30 ug/ml pyruvate kinase, and 10 ug/ml lactate dehydrogenase. 40 nM enzyme (374 kDa Gyr A2B2 from *E coli*) and a DMSO solution of the inhibitor to a final concentration of 4% were added and the reaction mixture allowed to incubate for 10 minutes at 30° C. The reaction was then started by the addition of ATP to a final concentration of 0.9 mM and the rate of NADH disappearance at 340 nm, measured over the course of 10 minutes. $K_i$ values were determined from rate versus. inhibitor concentration profiles.

Table 2 shows the activities of representative compounds tested in an *E. coli* gyrase $A_2B_2$ ATPase assay. Compounds having a $K_i$ less than 500 nM are rated "A", compounds having a $K_i$ between 500 nM and 1500 nM are rated "B" and compounds having a $K_i$ greater than 1500 nM are rated "C".

TABLE 2

Activity against *E. coli* gyrase

| No. | Activity | No. | Activity | No. | Activity |
|---|---|---|---|---|---|
| IA-1 | A | IA-2 | A | IA-15 | C |
| IA-18 | B | IA-22 | B | IA-23 | B |
| IA-24 | A | IA-25 | A | IA-28 | A |
| IA-29 | A | IA-30 | A | IA-31 | A |
| IA-32 | A | IA-33 | B | IA-34 | B |
| IA-35 | B | IA-36 | B | IA-37 | C |

TABLE 2-continued

Activity against *E. coli* gyrase

| No. | Activity | No. | Activity | No. | Activity |
|---|---|---|---|---|---|
| IA-38 | C | IA-39 | A | IA-40 | A |
| IA-41 | A | IA-42 | A | IA-43 | A |
| IA-44 | A | IA-46 | C | IA-66 | C |
| IA-67 | B | IA-68 | C | IA-69 | C |
| IB-28 | C | IB-29 | C | IB-30 | C |
| IB-31 | C | ID-28 | C | IE-22 | C |
| IE-23 | C | | | | |

While we have described a number of embodiments of this invention, it is apparent that our basic constructions may be altered to provide other embodiments which utilize the products and processes of this invention.

We claim:

1. A compound of formula IA:

IA

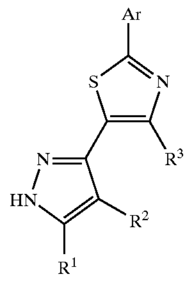

or a pharmaceutically acceptable salt thereof, wherein $R^1$ is an optionally substituted group selected from a $C_{1-6}$ aliphatic group, $—C(R^4)_2(CH_2)_nNRCOR$, $—C(R^4)=N—OR$, $—C(R^4)=N—OC(=O)(C_{1-6}$ aliphatic), $—C(R^4)=NNRCO_2(C_{1-6}$ aliphatic), $—C(R^4)=NNRCOR$, $—C(R^4)=NN(R)_2$, $—C(R^4)_2(CH_2)_nNRCO_2(C_{1-6}$ aliphatic), $—CO_2(C_{1-6}$ aliphatic), $—CON(R)_2$, $—C(R^4)_2(CH_2)_nCON(R)_2$, $—C(R^4)_2(CH_2)_nSO_2N(R)_2$, —CONH—OR, $—SO_2N(R)_2$, or $—C(R^4)_2(CH_2)_nNRSO_2(C_{1-6}$ aliphatic);

n is zero or one;

each R is independently selected from hydrogen or an optionally substituted $C_{1-6}$ aliphatic group;

$R^2$ is selected from hydrogen or, when $R^1$ is $—CO_2(C_{1-3}$ aliphatic) or $—CONH(C_{1-3}$ aliphatic), $R^2$ is further selected from -halo, —CN, $—C_{1-4}$ aliphatic, a three to five-membered heterocyclyl, or a five-membered heteroaryl;

Ring A is a heteroaryl ring selected from thiazole, oxazole, imidazole or pyrazole, wherein said imidazole is optionally attached by a $C_{1-3}$ bridge from an imidazole ring nitrogen to Ar to form a five- to seven-membered fused ring;

Z is $C—R^3$ or $N—R^3$;

$R^3$ is $—(CH_2)_pN(R^5)_2$ or an optionally substituted group selected from $C_{1-8}$ aliphatic, heterocyclyl, heterocyclylalkyl, aryl, aralkyl, heteroaryl, or heteroaralkyl;

each $R^4$ is indepependently selected from hydrogen, an optionally subtituted $C_{1-6}$ aliphatic group, or two $R^4$ taken together with the carbon to which they are attached form a three to six membered aliphatic ring;

each $R^5$ is independently selected from hydrogen, an optionally subtituted $C_{1-4}$ aliphatic group, or two $R^5$ taken together with the nitrogen to which they are attached form a five or six membered heterocyclic ring;

p is an integer from zero to four when Z is C—$R^3$ or an integer from one to four when Z is N—$R^3$; and Ar is an optionally substituted aryl, heteroaryl, or heterocyclyl ring.

2. The compound of claim 1 wherein said compound has one or more of the following features:

(a) $R^1$ is selected from —$C(R^4)_2NHCOR$, —$C(R^4)_2NHCO_2R$, —$CO_2R$, and —CONHR where R is an optionally substituted $C_{1-4}$ aliphatic group and each $R^4$ is independently selected from hydrogen, a $C_{1-3}$ alkyl group, or two $R^4$ taken together with the carbon to which they are attached form a three or four membered aliphatic ring; and/or (b) $R^3$ is a $C_{1-8}$ aliphatic optionally substituted by alkoxy, alkylamino or dialkylamino, optionally substituted morpholinyl, piperazinyl, piperidinyl, pyridyl, phenyl or benzyl; and/or (c) Ar is an optionally substituted ring selected from phenyl, pyridyl, or pyrimidinyl.

3. The compound of claim 2 wherein said compound has the following features:

(a) $R^1$ is selected from —$C(R^4)_2NHCOR$, —$C(R^4)_2NHCO_2R$, —$CO_2R$, and —CONHR where R is an optionally substituted $C_{1-4}$ aliphatic group and each $R^4$ is independently selected from hydrogen, a $C_{1-3}$ alkyl group, or two $R^4$ taken together with the carbon to which they are attached form a three or four membered aliphatic ring;

(b) $R^3$ is a $C_{1-8}$ aliphatic optionally substituted by alkoxy, alkylamino or dialkylamino, optionally substituted morpholinyl, piperazinyl, piperidinyl, pyridyl, phenyl or benzyl; and (c) Ar is an optionally substituted ring selected from phenyl, pyridyl, or pyrimidinyl.

4. The compound of claim 3 where R is selected from —$C_{1-4}$ alkyl, —$C_{1-4}$ haloalkyl, -allyl, —$CH_2C{\equiv}CR^6$, —$CH(C_{1-3}\ alkyl)C{\equiv}CR^6$, and —$C(Me)_2C{\equiv}CR^6$, and $R^6$ is selected from hydrogen, —$C_{1-4}$ aliphatic, —$CH_2N(Me)_2$, or —$CH_2O(C_{1-3}\ alkyl)$.

5. The compound of claim 4 wherein the compound is selected from compounds IA-1 through IA-70 listed in Table 1.

6. A pharmaceutical composition comprising a compound of claim 1 and a pharmaceutically acceptable carrier.

* * * * *